United States Patent
Chao et al.

(10) Patent No.: US 11,530,256 B2
(45) Date of Patent: Dec. 20, 2022

(54) **ANTIBODY SPECIFIC TO ALPHA-TOXIN OF *STAPHYLOCOCCAL AUREUS* AND USES THEREOF**

(71) Applicant: SYNERMORE BIOLOGICS (SUZHOU) CO., LTD., Suzhou (CN)

(72) Inventors: Tzu-Yuan Chao, Taipei (TW); Ching-Wen Chang, Taipei (TW); Eric Tsao, Taipei (TW)

(73) Assignee: SYNERMORE BIOLOGICS (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 17/211,506

(22) Filed: Mar. 24, 2021

(65) Prior Publication Data

US 2021/0317193 A1    Oct. 14, 2021

Related U.S. Application Data

(60) Provisional application No. 62/994,744, filed on Mar. 25, 2020.

(51) Int. Cl.
| | | |
|---|---|---|
| *A61K 39/395* | (2006.01) | |
| *C07K 16/12* | (2006.01) | |
| *A61P 31/04* | (2006.01) | |
| *G01N 33/569* | (2006.01) | |

(52) U.S. Cl.
CPC .......... *C07K 16/1267* (2013.01); *A61P 31/04* (2018.01); *G01N 33/56938* (2013.01); *C07K 2317/565* (2013.01); *C07K 2317/76* (2013.01); *C07K 2317/92* (2013.01); *G01N 2333/31* (2013.01)

(58) Field of Classification Search
CPC ................................................ C07K 16/1267
See application file for complete search history.

(56) References Cited

U.S. PATENT DOCUMENTS

2013/0164308 A1   6/2013   Foletti et al.
2021/0079071 A1   3/2021   Church

FOREIGN PATENT DOCUMENTS

| CN | 109384844 A | 2/2019 |
| CN | 110437334 A | 11/2019 |
| CN | 109400704 B | 7/2020 |
| EP | 2284193 A1 | 2/2011 |
| WO | 2012109285 A3 | 10/2012 |
| WO | 2013013323 A1 | 1/2013 |
| WO | 2016044588 A1 | 3/2016 |
| WO | 2018128973 A1 | 7/2018 |

OTHER PUBLICATIONS

Lloyd et al. Protein Engineering, Design & Selection 22:159-168,. (Year: 2009).*
Extended European Search Report for EP Application No. 21164842.3 dated Dec. 13, 2021.
Foletti Davide et al.: "Mechanism of Action andIn VivoEfficacy of a Human-Derived Antibody against*Staphylococcus aureus*[alpha]-Hemol", J. Molecular Biology, Academic Press, United Kingdom, vol. 425, No. 10, Feb. 13, 2013 (Feb. 13, 2013), pp. 1641-1654.
Partial European Search Report for EP Application No. 21164842.3 dated Nov. 10, 2021.
Ragle Brook et al: "Anti-alpha-hemolysin monoclonal antibodies mediate protection against *Staphylococcus aureus* pneumonia", Infection and Immunity, American Society for Microbiology, US, vol. 77, No. 7, Jul. 1, 2009 (Jul. 1, 2009), pp. 2712-2718.

* cited by examiner

*Primary Examiner* — Albert M Navarro
(74) *Attorney, Agent, or Firm* — Prosyla Group PC

(57) ABSTRACT

The present disclosure relates to an antibody or antigen-binding fragment thereof that specifically bind to α-toxin of *Staphylococcal aureus*. The present disclosure also relates to a pharmaceutical composition, a method for treating and/or preventing diseases and/or disorders caused by *Staphylococcal aureus* infection in a subject in need, and a method for detecting α-toxin of *Staphylococcal aureus* in a sample.

15 Claims, 16 Drawing Sheets

Specification includes a Sequence Listing.

```
                1         10         20         30         40         50         60
25A1-VH         QVKLQQSGPELVKPGASVKISCKAS GYSFTDYNMN WVKQSHGKSLEWIG SINPYYGITSYNQTFKG
IGHV1-2         QVQLVQSGAEVKKPGASVKVSCKAS GYTFTGYYMH WVRQAPGQGLEWMG WINPNSGGTNYAQKFQG
HU25A1-VH       QVQLVQSGAEVKKPGASVKVSCKAS GYSFTDYNMN WVRQAPGQGLEWMG SINPYYGITSYNQTFKG
HU25A1/VHB2     QVQLVQSGAEVKKPGASVKVSCKAS GYSFTDYNMN WVRQAPGQGLEWMG SINPYYGITSYNQTFKG
HU25A1/VHB5     QVQLVQSGAEVKKPGASVKVSCKAS GYSFTDYNMN WVRQAPGQGLEWMG SINPYYGITSYNQTFKG 70         80         90        100        110
25A1-VH         KATLTVDKSSSTAYMQLNSLTSEDSAVYYCAR IYYGDSLGLDY WGQGTTVTVSS
IGHV1-2         RVTMTRDTSISTAYMELSRLRSDDTAVYYCAR WGGDGFYAMDV WGQGTLVTVSS
HU25A1-VH       RVTMTRDTSISTAYMELSRLRSDDTAVYYCAR IYYGDSLGLDY WGQGTLVTVSS
HU25A1/VHB2     RVTITDKSISTAYMELSRLRSDDTAVYYCAR IYYGDSLGLDY WGQGTLVTVSS
HU25A1/VHB5     RVTITDTSISTAYMELSRLRSDDTAVYYCAR IYYGDSLGLDY WGQGTLVTVSS 1         10         20         30         40         50
25A1-VL         DIELTQSPAIMSASPGEKVTMTC SASSSVSYMH WYQQKSGTSPKRWIY DTSKLAS
IGVK3-11        EIVLTQSPATLSLSPGERATLSC RASQSVSSYLA WYQQKPGQAPRLLIY DASNRAT
HU25A1-VL       EIVLTQSPATLSLSPGERATLSC SASSSVSYMH WYQQKPGQAPRLLIY DTSKLAS
HU25A1/VLB4     EIVLTQSPATLSLSPGERATLSC SASSSVSYMH WYQQKPGQAPRRLIY DTSKLAS
HU25A1/VLB6     EIVLTQSPATLSLSPGERATLSC SASSSVSYMH WYQQKPGQAPRRLIY DTSKLAS 60         70         80         90        100
25A1-VL         GVPARFSGSGSGTSYSLTISSMEAEDAATYYC QQWSSNPLT FGAGTKLEIKR
IGVK3-11        GIPARFSGSGSGTDFTLTISSLEPEDFAVYYC QQRSNWP--- FGQGTKVEIKR
HU25A1-VL       GIPARFSGSGSGTDFTLTISSLEPEDFAVYYC QQWSSNPLT FGQGTKVEIKR
HU25A1/VLB4     GIPARFSGSGSGTDFTLTISSLEPEDFAVYYC QQWSSNPLT FGQGTKVEIKR
HU25A1/VLB6     GIPARFSGSGSGTDFTLTISSLEPEDFAVYYC QQWSSNPLT FGQGTKVEIKR
```

Figure 3(A)

25A1-B5B6AQT Heavy chain:
DPKGSLSWRILLFLSLAFELSYGQVQLVQSGAEVKKPGASVKVSCKASGYSFTDYNMNWVRQAPGQGL
EWMGSINPYYGITSYAQTFKGRVTLTVDTSISTAYMELSRLRSDDTAVYYCARIYYGDSLGLDYWGQG
TLVTVSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPG*

25A1-B5B6AQT Light chain:
METDTLLLWVLLLWVPGSTGEIVLTQSPATLSLSPGERATLSCSASSSVSYMHWYQQKPGQAPRRLIY
DTSKLASGIPARFSGSGSGTDFTLTISSLEPEDFAVYYCQQWSSNPLTFGQGTKVEIKRTVAAPSVFI
FPPSDEQLKSGTASVVCLLNNFYPREAKVQWKVDNALQSGNSQESVTEQDSKDSTYSLSSTLTLSKAD
YEKHKVYACEVTHQGLSSPVTKSFNRGEC*

Figure 3(C)

```
                        SEQUENCE LISTING

<160> NUMBER OF SEQ ID NOS: 31

<210> SEQ ID NO 1
<211> LENGTH: 10
<212> TYPE: PRT
<213> ORGANISM: mouse

<400> SEQUENCE: 1

Gly Tyr Ser Phe Thr Asp Tyr Asn Met Asn
1               5                   10

<210> SEQ ID NO 2
<211> LENGTH: 10
<212> TYPE: PRT
<213> ORGANISM: mouse

<400> SEQUENCE: 2

Gly Tyr Ser Phe Thr Gly Tyr Phe Met Asn
1               5                   10

<210> SEQ ID NO 3
<211> LENGTH: 17
<212> TYPE: PRT
<213> ORGANISM: mouse

<400> SEQUENCE: 3

Ser Ile Asn Pro Tyr Tyr Gly Ile Thr Ser Tyr Asn Gln Thr Phe Lys
1               5                   10                  15

Gly

<210> SEQ ID NO 4
<211> LENGTH: 17
<212> TYPE: PRT
<213> ORGANISM: mouse

<400> SEQUENCE: 4

Ser Ile Asn Pro His Tyr Gly Ile Thr Ser Tyr Asn Gln Thr Phe Lys
1               5                   10                  15

Gly

<210> SEQ ID NO 5
<211> LENGTH: 17
<212> TYPE: PRT
<213> ORGANISM: mouse

<400> SEQUENCE: 5

Ser Ile Asn Pro Tyr Tyr Gly Ile Thr Thr Tyr Asn Gln Thr Phe Lys
1               5                   10                  15

Gly

<210> SEQ ID NO 6
<211> LENGTH: 17
<212> TYPE: PRT
<213> ORGANISM: mouse

<400> SEQUENCE: 6

Arg Ile Asn Pro Tyr Asn Gly Asp Thr Leu Tyr Lys Gln Asn Phe Lys
```

```
1               5                   10                  15

Asp

<210> SEQ ID NO 7
<211> LENGTH: 11
<212> TYPE: PRT
<213> ORGANISM: mouse

<400> SEQUENCE: 7

Ile Tyr Tyr Gly Asp Ser Leu Gly Leu Asp Tyr
1               5                   10

<210> SEQ ID NO 8
<211> LENGTH: 11
<212> TYPE: PRT
<213> ORGANISM: mouse

<400> SEQUENCE: 8

Asp Gly Asp Gly Tyr Tyr Tyr Ala Met Asp Tyr
1               5                   10

<210> SEQ ID NO 9
<211> LENGTH: 11
<212> TYPE: PRT
<213> ORGANISM: mouse

<400> SEQUENCE: 9

Val Tyr Tyr Gly Asp Ser Leu Gly Leu Asp Tyr
1               5                   10

<210> SEQ ID NO 10
<211> LENGTH: 10
<212> TYPE: PRT
<213> ORGANISM: mouse

<400> SEQUENCE: 10

Ser Ala Ser Ser Ser Val Ser Tyr Met His
1               5                   10

<210> SEQ ID NO 11
<211> LENGTH: 10
<212> TYPE: PRT
<213> ORGANISM: mouse

<400> SEQUENCE: 11

Ser Ala Ser Ser Ser Ile Ser Tyr Met His
1               5                   10

<210> SEQ ID NO 12
<211> LENGTH: 10
<212> TYPE: PRT
<213> ORGANISM: mouse

<400> SEQUENCE: 12

Ser Ala Ser Ser Ser Lys Ser Tyr Ile His
1               5                   10

<210> SEQ ID NO 13
<211> LENGTH: 10
<212> TYPE: PRT
<213> ORGANISM: mouse

<400> SEQUENCE: 13

Ser Ala Ser Ser Ser Val Ser Tyr Met Tyr
```

```
1               5                   10
```

<210> SEQ ID NO 14
<211> LENGTH: 7
<212> TYPE: PRT
<213> ORGANISM: mouse

<400> SEQUENCE: 14

```
Asp Thr Ser Lys Leu Ala Ser
1               5
```

<210> SEQ ID NO 15
<211> LENGTH: 7
<212> TYPE: PRT
<213> ORGANISM: mouse

<400> SEQUENCE: 15

```
Asp Thr Ser Asn Leu Ala Ser
1               5
```

<210> SEQ ID NO 16
<211> LENGTH: 9
<212> TYPE: PRT
<213> ORGANISM: mouse

<400> SEQUENCE: 16

```
Gln Gln Trp Ser Ser Asn Pro Leu Thr
1               5
```

<210> SEQ ID NO 17
<211> LENGTH: 9
<212> TYPE: PRT
<213> ORGANISM: mouse

<400> SEQUENCE: 17

```
Gln Gln Trp Ser Ser Asn Pro Pro Thr
1               5
```

<210> SEQ ID NO 18
<211> LENGTH: 9
<212> TYPE: PRT
<213> ORGANISM: mouse

<400> SEQUENCE: 18

```
His Gln Arg Ser Ser Tyr Pro Trp Thr
1               5
```

<210> SEQ ID NO 19
<211> LENGTH: 120
<212> TYPE: PRT
<213> ORGANISM: mouse

<400> SEQUENCE: 19

```
Gln Val Lys Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
                20                  25                  30

Asn Met Asn Trp Val Lys Gln Ser His Gly Lys Ser Leu Glu Trp Ile
            35                  40                  45

Gly Ser Ile Asn Pro Tyr Tyr Gly Ile Thr Ser Tyr Asn Gln Thr Phe
        50                  55                  60

Lys Gly Lys Ala Thr Leu Thr Val Asp Lys Ser Ser Ser Thr Ala Tyr
65                  70                  75                  80
```

```
Met Gln Leu Asn Ser Leu Thr Ser Glu Asp Ser Ala Val Tyr Tyr Cys
            85                  90                  95

Ala Arg Ile Tyr Tyr Gly Asp Ser Leu Gly Leu Asp Tyr Trp Gly Gln
            100                 105                 110

Gly Thr Thr Val Thr Val Ser Ser
        115                 120

<210> SEQ ID NO 20
<211> LENGTH: 107
<212> TYPE: PRT
<213> ORGANISM: mouse

<400> SEQUENCE: 20

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Leu Thr
                85                  90                  95

Phe Gly Ala Gly Thr Lys Leu Glu Ile Lys Arg
            100                 105

<210> SEQ ID NO 21
<211> LENGTH: 120
<212> TYPE: PRT
<213> ORGANISM: Artificial Sequence
<220> FEATURE:
<223> OTHER INFORMATION: humanized antibody

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Ser Ile Asn Pro Tyr Tyr Gly Ile Thr Ser Tyr Asn Gln Thr Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Tyr Tyr Gly Asp Ser Leu Gly Leu Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
```

<223> OTHER INFORMATION: humanized antibody

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Ser Ile Asn Pro Tyr Tyr Gly Ile Thr Ser Tyr Asn Gln Thr Phe
    50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Tyr Tyr Gly Asp Ser Leu Gly Leu Asp Tyr Trp Gly Gln
            100                 105                 110

Gly Thr Leu Val Thr Val Ser Ser
        115                 120

<210> SEQ ID NO 23
<211> LENGTH: 120
<212> TYPE: PRT
<213> ORGANISM: Artificial Sequence
<220> FEATURE:
<223> OTHER INFORMATION: humanized antibody

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Ser Ile Asn Pro Tyr Tyr Gly Ile Thr Ser Tyr Asn Gln Thr Phe
    50                  55                  60

Lys Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Tyr Tyr Gly Asp Ser Leu Gly Leu Asp Tyr Trp Gly Gln
            100                 105                 110

Gly Thr Leu Val Thr Val Ser Ser
        115                 120

<210> SEQ ID NO 24
<211> LENGTH: 107
<212> TYPE: PRT
<213> ORGANISM: Artificial Sequence
<220> FEATURE:
<223> OTHER INFORMATION: humanized antibody

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr

```
                35                  40                  45
Asp Thr Ser Lys Leu Ala Ser Gly Ile Pro Ala Arg Phe Ser Gly Ser
         50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gln Gly Thr Lys Val Glu Ile Lys Arg
             100                 105

<210> SEQ ID NO 25
<211> LENGTH: 107
<212> TYPE: PRT
<213> ORGANISM: Artificial Sequence
<220> FEATURE:
<223> OTHER INFORMATION: humanized antibody

<400> SEQUENCE: 25

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Val Ser Tyr Met
                 20                  25                  30

His Trp Tyr Gln Gln Lys Pro Gly Gln Ala Pro Arg Arg Trp Ile Tyr
             35                  40                  45

Asp Thr Ser Lys Leu Ala Ser Gly Ile Pro Ala Arg Phe Ser Gly Ser
         50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gln Gly Thr Lys Val Glu Ile Lys Arg
             100                 105

<210> SEQ ID NO 26
<211> LENGTH: 107
<212> TYPE: PRT
<213> ORGANISM: Artificial Sequence
<220> FEATURE:
<223> OTHER INFORMATION: humanized antibody

<400> SEQUENCE: 26

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Val Ser Tyr Met
                 20                  25                  30

His Trp Tyr Gln Gln Lys Pro Gly Gln Ala Pro Arg Arg Leu Ile Tyr
             35                  40                  45

Asp Thr Ser Lys Leu Ala Ser Gly Ile Pro Ala Arg Phe Ser Gly Ser
         50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gln Gly Thr Lys Val Glu Ile Lys Arg
             100                 105

<210> SEQ ID NO 27
<211> LENGTH: 120
```

```
<212> TYPE: PRT
<213> ORGANISM: Artificial Sequence
<220> FEATURE:
<223> OTHER INFORMATION: humanized antibody

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
        35                  40                  45

Gly Ser Ile Asn Pro Tyr Tyr Gly Ile Thr Ser Tyr Ala Gln Thr Phe
50                  55                  60

Lys Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Tyr Tyr Gly Asp Ser Leu Gly Leu Asp Tyr Trp Gly Gln
            100                 105                 110

Gly Thr Leu Val Thr Val Ser Ser
        115                 120

<210> SEQ ID NO 28
<211> LENGTH: 106
<212> TYPE: PRT
<213> ORGANISM: Artificial Sequence
<220> FEATURE:
<223> OTHER INFORMATION: humanized antibody

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Ile Pro Ala Arg Phe Ser Gly Ser
50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 29
<211> LENGTH: 120
<212> TYPE: PRT
<213> ORGANISM: Artificial Sequence
<220> FEATURE:
<223> OTHER INFORMATION: humanized antibody

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Met Asn Trp Val Arg Gln Ala Pro Gly Gln Gly Leu Glu Trp Met
```

```
                35                  40                  45
Gly Ser Ile Asn Pro Tyr Tyr Gly Ile Thr Ser Tyr Ala Gln Thr Phe
        50                  55                  60

Lys Gly Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ile Tyr Tyr Gly Asp Ser Leu Gly Leu Asp Tyr Trp Gly Gln
            100                 105                 110

Gly Thr Leu Val Thr Val Ser Ser
            115                 120

<210> SEQ ID NO 30
<211> LENGTH: 106
<212> TYPE: PRT
<213> ORGANISM: Artificial Sequence
<220> FEATURE:
<223> OTHER INFORMATION: humanized antibody

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
                20                  25                  30

His Trp Tyr Gln Gln Lys Pro Gly Gln Ala Pro Arg Arg Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 31
<211> LENGTH: 17
<212> TYPE: PRT
<213> ORGANISM: mouse

<400> SEQUENCE: 31

Ser Ile Asn Pro Tyr Tyr Gly Ile Thr Ser Tyr Asn Gln Thr Phe Arg
1               5                   10                  15

Gly
```

ANTIBODY SPECIFIC TO ALPHA-TOXIN OF *STAPHYLOCOCCAL AUREUS* AND USES THEREOF

This application claims benefit to and priority of U.S. Provisional Patent Application No. 62/994,744, filed Mar. 25, 2020, and entitled, "ANTIBODY SPECIFIC TO ALPHA-TOXIN OF *STAPHYLOCOCCAL AUREUS* AND USES THEREOF," the contents of which is referenced in its entirety.

The instant application contains a Sequence Listing which has been filed electronically in ASCII format and is hereby incorporated by reference in its entirety. Said ASCII copy, created on Mar. 23, 2021, is named G4590-07900US_Seq-Listing.txt and is 16 kilobytes in size.

FIELD OF THE DISCLOSURE

The present disclosure relates to an antibody or antigen-binding fragment thereof, which is specific to α-toxin of *Staphylococcal aureus*, and uses thereof.

BACKGROUND OF THE DISCLOSURE

*Staphylococcus aureus* is an opportunistic pathogen often carried asymptomatically on the human body. Pathogenic strains often promote infections by producing potent protein toxins and other virulent factors that evade the human immune system. *S. aureus* can cause a range of illnesses, from minor skin infections to life-threatening diseases, such as pneumonia, meningitis, osteomyelitis, endocarditis, toxic shock syndrome, bacteremia, and sepsis. It is still one of the five most common cause of nosocomial infections and is often the cause of postsurgical wound infections.

The emergence of antibiotic-resistant forms of *S. aureus* such as Methicillin-resistant *Staphylococcus aureus* (MRSA) is a worldwide problem in clinical medicine. Current concepts on the virulence mechanisms of MRSA include a remarkable array of cell-surface and secreted virulence factors. The cell-surface virulence factors include microbial surface components recognizing adhesive matrix molecules (MSCRAMMs), iron-regulated proteins, polysaccharide intercellular adhesion, and capsular polysaccharides. The secreted virulence factors are typically produced during post-exponential and stationary phase, and they include exoenzymes, exotoxins α, β, γ, and δ toxins, Panton-Valentine leukocidin (PVL), superantigens, and toxic shock syndrome toxin-1 (TSST-1), and exfoliative toxins A and B. US 20210079071 provides monoclonal antibody inhibitors of coagulases staphylocoagulase and vWbp for treatment of *Staphylococcus aureus*.

Alpha-toxin (AT) is a cytolytic pore-forming toxin that is conserved among *S. aureus* clinical isolates and has been shown to play a role in pneumonia, dermonecrosis, endocarditis, and sepsis. AT is secreted as a 33 kDa soluble monomeric protein which can assemble into a ring structure on the surface of eukaryotic cells. The assembled toxin inserts into the cell membrane, forming a pore that contribute to cellular injury and death by disrupting the integrity of the membrane. Toxins as targets for immunoprophylaxis have been successful for decades as part of vaccines or passive immunotherapy against bacterial diseases such as diphtheria, tetanus, and botulism. Unlike active immunization, which sometimes requires repeated boosters and long periods of time for maximum immune responses to be generated, passive immunization would provide immediate treatment for unvaccinated patients to help reduce the severity of acute *S. aureus* disease.

Thus, there is need for developing a novel approach to treating or preventing *S. aureus* infection.

SUMMARY OF THE DISCLOSURE

The present disclosure provides an antibody or antigen-binding fragment thereof that specifically binds to an epitope in α-toxin of *Staphylococcal aureus* or a fragment thereof. The antibody according to the disclosure neutralizes α-toxin of *Staphylococcal aureus* and is thus useful for treating and/or preventing diseases and/or disorders caused by *Staphylococcal aureus* infection. The antibody of the disclosure is also useful for detecting α-toxin of *Staphylococcal aureus*.

The present disclosure provides a pharmaceutical composition comprising the antibody or antigen-binding fragment thereof as mentioned above and pharmaceutically acceptable carriers or excipients.

The present disclosure provides a method for treating and/or preventing diseases and/or disorders caused by *Staphylococcal aureus* infection in a subject in need, comprising administering to the subject a pharmaceutical composition comprising the antibody or antigen-binding fragment thereof as mentioned above.

The present disclosure provides a method for detecting α-toxin of *Staphylococcal aureus* in a sample comprising contacting the sample with the antibody or antigen-binding fragment thereof as mentioned above.

The present disclosure also provides a kit for detecting α-toxin of *Staphylococcal aureus* in a sample, comprising an antibody described herein or antigen-binding fragment thereof.

The present disclosure is described in detail in the following sections. Other characteristics, purposes and advantages of the present disclosure can be found in the detailed description and claims.

BRIEF DESCRIPTION OF THE DRAWINGS

FIG. 3(A) Amino acid sequence of various anti-α-toxin $V_H$ and $V_L$ domain. Human germline sequences IGHV1-2 and IGVK3-11 were used for grafting. The difference in amino acid between murine antibody and human germline sequence are shown in bold and underlined; CDR residues are shown in box; the back-mutations are shown with grey labeled. FIG. 3(C) Amino acid sequence of 25A1-B5B6AQT. Amino acid sequence of signal peptide represents in bold and underlined; variable regions are labeled in grey.

FIG. 10 (B) Lung inflammation was evaluated in terms of macroscopic scores for all treatment groups, with higher score indicating more severe damage due to bacterial infection. Open circles represent dead animals by 30 hours post infection. Filled circles represent live animals by 30 hours post infection. FIG. 10 (C) Ratios of lung weight (LW) over body weight (BW). FIG. 10 (D) Bacterial counts in the lung tissue. p-value<0.0083 indicates significance.

DETAILED DESCRIPTION OF THE DISCLOSURE

Figure 1:
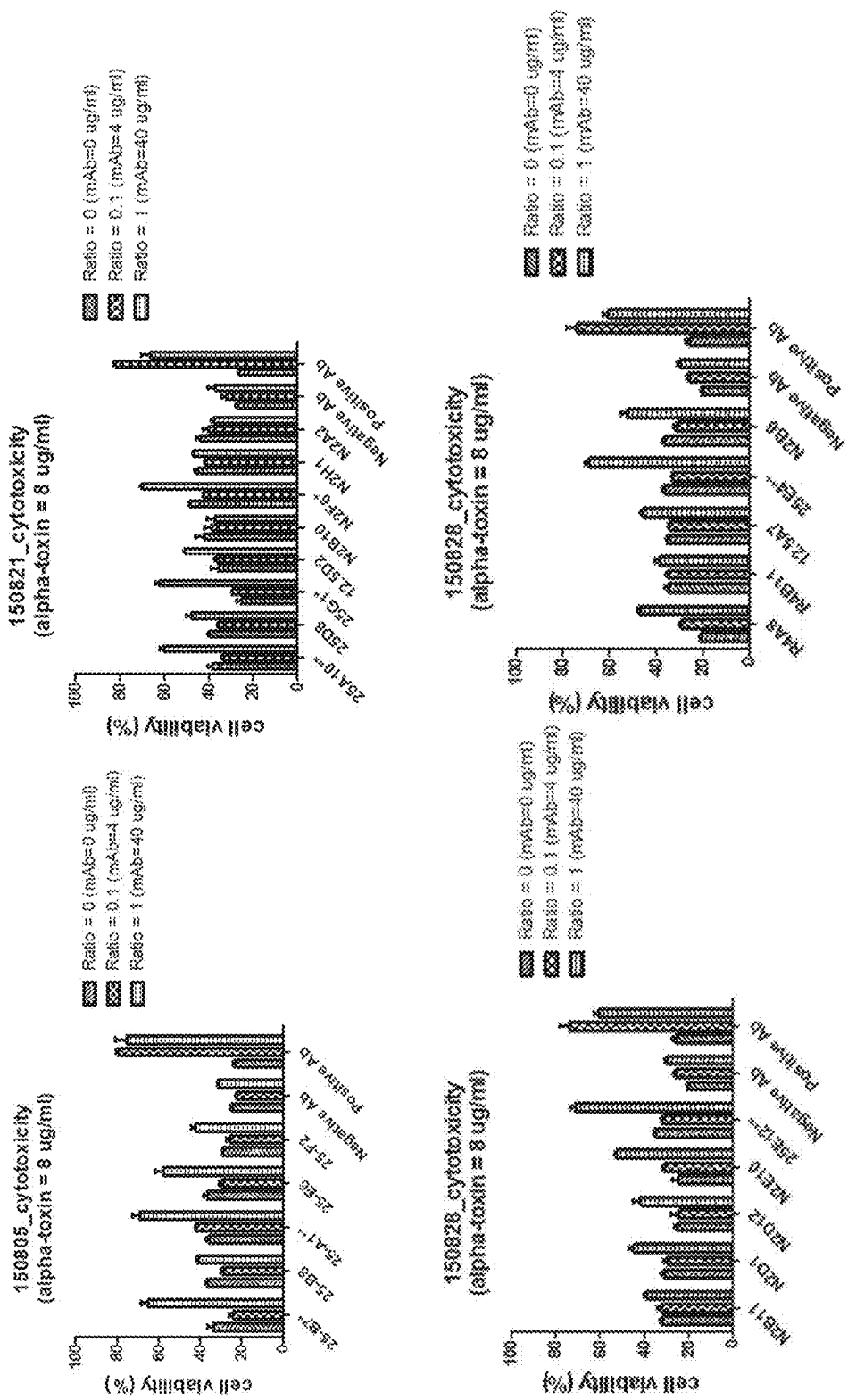
FIG. 1: Anti-α-toxin monoclonal antibodies increased the cell viability of A549 cells in the presence of α-toxin. Purified antibodies at the concentration of 4 and 40 μg/ml were added in the cytolytic assay in the presence of 8 μg/ml of α-toxin to obtain α-toxin to antibody ratio of 1:0.1 (4 μg/ml) or 1:1 (40 μg/ml). Cell viability was analyzed using a colorimetric MTT assay kit. "*" The antibody showed the ability to prevent α-toxin-induced cell lysis.
Figure 1:
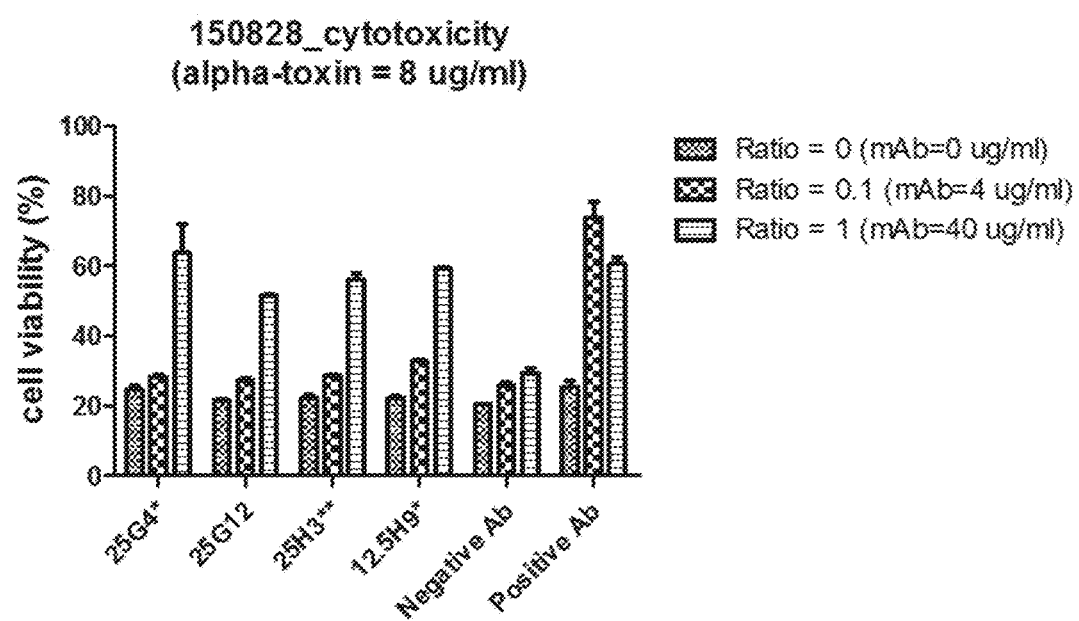

The present disclosure provides an antibody or antigen-binding fragment thereof that specifically binds to an epitope in α-toxin of Staphylococcal aureus or a fragment thereof.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

As used herein, the term "epitope" refers to the site on the antigen to which an antibody binds.

The term "antibody", as used herein, means any antigen-binding molecule or molecular complex comprising at least one complementarity determining region (CDR) that specifically binds to or interacts with a particular antigen (e.g., α-toxin). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-α-toxin antibody (or antigen-binding portion thereof) may be identical to the human germline sequences, or may be naturally or artificially modified. An amino acid consensus sequence may be defined based on a side-by-side analysis of two or more CDRs.

The term "monoclonal antibody" as used herein is not limited to antibodies produced through hybridoma technology. A monoclonal antibody is derived from a single clone, including any eukaryotic, prokaryotic, or phage clone, by any means available or known in the art.

The term "chimeric" antibody as used herein refers to an antibody having variable sequences derived from a non-human immunoglobulin and human immunoglobulin constant regions, typically chosen from a human immunoglobulin template.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of an antibody that, when administered to a mammal or other subject for treating a disease, is sufficient to effect such treatment for the disease.

As used herein, the term "sample" encompasses a variety of sample types obtained from an individual, subject or patient and can be used in a diagnostic or monitoring assay. The definition encompasses blood and other liquid samples of biological origin, solid tissue samples such as a biopsy specimen or tissue cultures or cells derived therefrom and the progeny thereof.

The present disclosure develops a monoclonal antibody that specifically neutralizes α-toxin, thus providing passive immunotherapy in the context of S. aureus infections. The passive immunization would provide immediate treatment for unvaccinated patients to help reduce the severity of acute S. aureus disease. Functionally, the antibodies of the present disclosure exhibit significant inhibitory activities to AT-induced cytotoxicity and showed strong in vivo efficacies in preventing, prophylactic treating and/or treating infection of S. aureus and/or pneumonia.

Particularly, the antibody or antigen-binding fragment thereof comprises complementarity determining regions (CDRs) of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, and wherein:

the CDRH1 region comprises the amino acid sequence selected from the group consisting of SEQ ID NOs: 1 to 2 or a substantially similar sequence thereof; the CDRH2 region comprises the amino acid sequence selected from the group consisting of SEQ ID NOs: 3 to 6 and 31 or a substantially similar sequence thereof; the CDRH3 region comprises the amino acid sequence selected from the group consisting of SEQ ID NOs: 7 to 9 or a substantially similar sequence thereof; and the CDRL1 region comprises the amino acid sequence selected from the group consisting of SEQ ID NOs: 10 to 13 or a substantially similar sequence thereof; the CDRL2 region comprises the amino acid sequence selected from the group consisting of SEQ ID NOs: 14 to 15 or a substantially similar sequence thereof; the CDRL3 region comprises the amino acid sequence selected from the group consisting of SEQ ID NOs: 16 to 18 or a substantially similar sequence thereof.

The sequence listing is shown in Table 1.

TABLE 1

| SEQ ID No. | Name | Sequence |
|---|---|---|
| 1 | 25A1 CDRH1 | GYSFTDYNMN |
| 2 | 25G1 CDRH1 | GYSFTGYFMN |
| 3 | 25A1 CDRH2 | SINPYYGITSYNQTFKG |
| 4 | 25E12 CDRH2 | SINPHYGITSYNQTFKG |
| 5 | 25H3 CDRH2 | SINPYYGITTYNQTFKG |
| 6 | 25G1 CDRH2 | RINPYNGDTLYKQNFKD |
| 7 | 25A1 CDRH3 | IYYGDSLGLDY |
| 8 | 25G1 CDRH3 | DGDGYYYAMDY |
| 9 | 5H9 CDRH3 | VYYGDSLGLDY |
| 10 | 25A1 CDRL1 | SASSSVSYMH |
| 11 | 25A10 CDRL1 | SASSSISYMH |
| 12 | 25B7 CDRL1 | SASSSKSYIH |

TABLE 1-continued

| SEQ ID No. | Name | Sequence |
|---|---|---|
| 13 | 5H9 CDRL1 | SASSSVSYMY |
| 14 | 25A1 CDRL2 | DTSKLAS |
| 15 | 5H9 CDRL2 | DTSNLAS |
| 16 | 25A1 CDRL3 | QQWSSNPLT |
| 17 | 25A10 CDRL3 | QQWSSNPPT |
| 18 | 25G1 CDRL3 | HQRSSYPWT |
| 19 | 25A1 heavy chain variable region | QVKLQQSGPELVKPGASVKISCKASGYSFTDYNMNWV KQSHGKSLEWIGSINPYYGITSYNQTFKGKATLTVDKSS STAYMQLNSLTSEDSAVYYCARIYYGDSLGLDYWGQG TTVTVSS |
| 20 | 25A1 light chain variable region | DIELTQSPAIMSASPGEKVTMTCSASSSVSYMHYQQK SGTSPKRWIYDTSKLASGVPARFSGSGSGTSYSLTISSME AEDAATYYCQQWSSNPLTFGAGTKLEIKR |
| 21 | HU25A1/VH | QVQLVQSGAEVKKPGASVKVSCKASGYSFTDYNMNW VRQAPGQGLEWMGSINPYYGITSYNQTFKGRVTMTRDT SISTAYMELSRLRSDDTAVYYCARIYYGDSLGLDYWGQ GTLVTVSS |
| 22 | HU25A1/VHB2 | QVQLVQSGAEVKKPGASVKVSCKASGYSFTDYNMNW VRQAPGQGLEWMGSINPYYGITSYNQTFKGRVTLTVDK SISTAYMELSRLRSDDTAVYYCARIYYGDSLGLDYWGQ GTLVTVSS |
| 23 | HU25A1/VHB5 | QVQLVQSGAEVKKPGASVKVSCKASGYSFTDYNMNW VRQAPGQGLEWMGSINPYYGITSYNQTFKGRVTLTVDT SISTAYMELSRLRSDDTAVYYCARIYYGDSLGLDYWGQ GTLVTVSS |
| 24 | HU25A1/VL | EIVLTQSPATLSLSPGERATLSCSASSSVSYMHWYQQKP GQAPRLLIYDTSKLASGIPARFSGSGSGTDFTLTISSLEPE DFAVYYCQQWSSNPLTFGQGTKVEIKR |
| 25 | HU25A1/VLB4 | EIVLTQSPATLSLSPGERATLSCSASSSVSYMHWYQQKP GQAPRRWIYDTSKLASGIPARFSGSGSGTDFTLTISSLEPE DFAVYYCQQWSSNPLTFGQGTKVEIKR |
| 26 | HU25A1/VLB6 | EIVLTQSPATLSLSPGERATLSCSASSSVSYMHWYQQKP GQAPRRLIYDTSKLASGIPARFSGSGSGTDFTLTISSLEPE DFAVYYCQQWSSNPLTFGQGTKVEIKR |
| 27 | 25A1-B2B4AQT/VH (humanized antibody) | QVQLVQSGAEVKKPGASVKVSCKASGYSFTDYNMNW VRQAPGQGLEWMGSINPYYGITSYAQTFKGRVTLTVDK SISTAYMELSRLRSDDTAVYYCARIYYGDSLGLDYWGQ GTLVTVSS |
| 28 | 25A1-B2B4AQT/VL (humanized antibody) | EIVLTQSPATLSLSPGERATLSCSASSSVSYMHWYQQKP GQAPRRWIYDTSKLASGIPARFSGSGSGTDFTLTISSLEPE DFAVYYCQQWSSNPLTFGQGTKVEIK |
| 29 | 25A1-B5B6AQT/VH (humanized antibody) | QVQLVQSGAEVKKPGASVKVSCKASGYSFTDYNMNW VRQAPGQGLEWMGSINPYYGITSYAQTFKGRVTLTVDT SISTAYMELSRLRSDDTAVYYCARIYYGDSLGLDYWGQ GTLVTVSS |
| 30 | 25A1-B5B6AQT/VL (humanized antibody) | EIVLTQSPATLSLSPGERATLSCSASSSVSYMHWYQQKP GQAPRRLIYDTSKLASGIPARFSGSGSGTDFTLTISSLEPE DFAVYYCQQWSSNPLTFGQGTKVEIK |
| 31 | 25E4 CDRH2 | SINPYYGITSYNQTFRG |

The antibody according to the disclosure can be full-length (for example, an IgG1 or IgG4 antibody) or may comprise only an antigen-binding portion (for example, a Fab, F(ab')2 or scFv fragment), and may be modified to affect functionality as needed.

The antibody or antigen-binding fragment thereof according to the disclosure specifically binds to α-toxin of *Staphylococcal aureus*. As a cytolytic pore-forming toxin, α-toxin is conserved among *S. aureus* clinical isolates. Alpha-toxin is a 33 kDa soluble monomeric protein which can assemble into a ring structure on the surface of eukaryotic cells and then the assembled toxin inserts into the cell membrane, forming a pore that contribute to cellular injury and death by disrupting the integrity of the membrane.

The present disclosure includes an anti-α-toxin antibody and antigen-binding fragment thereof that binds monomeric or the ring structure of α-toxin molecules with high affinity.

Various techniques known to persons of ordinary skill in the art can be used to determine whether an antibody "specifically binds to one or more amino acids" within a polypeptide or protein. Exemplary techniques include, e.g., routine cross-blocking assay such as that described Antibodies, Harlow and Lane (Cold Spring Harbor Press, Cold Spring Harb., N. Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody specifically binds is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

The present disclosure further includes an anti-α-toxin antibody that specifically binds to the same epitope.

One can easily determine whether an antibody specifically binds to the same epitope as, or competes for binding with, a reference anti-α-toxin antibody by using routine methods known in the art. For example, to determine if a test antibody binds to the same epitope as a reference anti-α-toxin antibody of the disclosure, the reference antibody is allowed to bind to an α-toxin protein (e.g., a monomeric or the ring structure of α-toxin). Next, the ability of a test antibody to bind to the α-toxin molecule is assessed. If the test antibody is able to bind to α-toxin following saturation binding with the reference anti-α-toxin antibody, it can be concluded that the test antibody binds to a different epitope than the reference anti-α-toxin antibody. On the other hand, if the test antibody is not able to bind to the α-toxin molecule following saturation binding with the reference anti-α-toxin antibody, then the test antibody may bind to the same epitope as the epitope bound by the reference anti-α-toxin antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay. Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

The term "antibody", as used herein, also includes an antigen-binding fragment of a full antibody molecule. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment includes: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide.

Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$; (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

In one preferred embodiment, the antibody or antigen-binding fragment thereof according to the disclosure is a mammalian antibody.

The term "mammalian antibody", as used herein, is intended to include antibodies having variable and constant regions derived from mammalian germline immunoglobulin sequences. The mammalian antibodies of the disclosure may include amino acid residues not encoded by mammalian germline immunoglobulin sequences (e.g., mutations introduced by random or site-specific mutagenesis in vitro or by somatic mutation in vivo), for example in the CDRs and in particular CDR3.

The term "recombinant mammalian antibody", as used herein, is intended to include all mammalian antibodies that are prepared, expressed, created or isolated by recombinant means, such as antibodies expressed using a recombinant expression vector transfected into a host cell (described further below), antibodies isolated from a recombinant, combinatorial mammalian antibody library (described further below), antibodies isolated from an animal (e.g., a mouse) that is transgenic for mammalian immunoglobulin genes or antibodies prepared, expressed, created or isolated by any other means that involves splicing of mammalian immunoglobulin gene sequences to other DNA sequences. Such recombinant mammalian antibodies have variable and constant regions derived from mammalian germline immunoglobulin sequences.

In certain embodiments, however, such recombinant mammalian antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the mammalian antibody germline repertoire in vivo.

Mammalian antibodies such as human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The anti-α-toxin antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The present disclosure also includes an anti-α-toxin antibody comprising variants of any of the $V_H$, $V_L$, and/or CDR amino acid sequences disclosed herein having one or more conservative substitutions. For example, the present disclosure includes an anti-α-toxin antibody having $V_H$, $V_L$, and/or CDR amino acid sequences with, e.g., 10 or fewer, 8 or fewer, 6 or fewer, 4 or fewer, etc. conservative amino acid substitutions relative to any of the $V_H$, $V_L$, and/or CDR amino acid sequences disclosed herein.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least about 95% sequence identity, even more preferably at least about 98% or 99% sequence identity. In one preferred embodiment, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

In one preferred embodiment of the disclosure, the antibody or antigen-binding fragment thereof comprises complementarity determining regions of a heavy chain variable region and complementarity determining regions of a light chain variable region, wherein the complementarity determining regions of the heavy chain variable region comprises CDRH1, CDRH2 and CDRH3 regions, and the complementarity determining regions of the light chain variable region comprises CDRL1, CDRL2 and CDRL3 regions, the CDRH1 region comprises the amino acid sequence selected from the group consisting of SEQ ID NOs: 1 to 2 or a substantially similar sequence thereof having at least about 90%, at least about 95%, at least about 98% or at least about 99% sequence identity;

the CDRH2 region comprises the amino acid sequence selected from the group consisting of SEQ ID NOs: 3 to 6 and 31 or a substantially similar sequence thereof having at least about 90%, at least about 95%, at least about 98% or at least about 99% sequence identity;

the CDRH3 region comprises the amino acid sequence selected from the group consisting of SEQ ID NOs: 7 to 9 or a substantially similar sequence thereof having at least about 90%, at least about 95%, at least about 98% or at least about 99% sequence identity;

the CDRL1 region comprises the amino acid sequence selected from the group consisting of SEQ ID NOs: 10 to 13 or a substantially similar sequence thereof having at least about 90%, at least about 95%, at least about 98% or at least about 99% sequence identity;

the CDRL2 region comprises the amino acid sequence selected from the group consisting of SEQ ID NOs: 14 to 15 or a substantially similar sequence thereof having at least about 90%, at least about 95%, at least about 98% or at least about 99% sequence identity;

and the CDRL3 region comprises the amino acid sequence selected from the group consisting of SEQ ID NOs: 16 to 18 or a substantially similar sequence thereof having at least about 90%, at least about 95%, at least about 98% or at least about 99% sequence identity.

In one preferred embodiment of the disclosure, the antibody or antigen-binding fragment thereof comprises complementarity determining regions of a heavy chain variable region and complementarity determining regions of a light chain variable region as shown in Table 2.

TABLE 2

| Clone | CDRH1 (SEQ ID NO.) | CDRH2 (SEQ ID NO.) | CDRH3 (SEQ ID NO.) |
|---|---|---|---|
| 25A1 | GYSFTDYNMN (1) | SINPYYGITSYNQTFKG (3) | IYYGDSLGLDY (7) |
| 25A10 | GYSFTDYNMN (1) | SINPYYGITSYNQTFKG (3) | IYYGDSLGLDY (7) |
| 25E4 | GYSFTDYNMN (1) | SINPYYGITSYNQTFRG (31) | IYYGDSLGLDY (7) |
| 25E12 | GYSFTDYNMN (1) | SINPHYGITSYNQTFKG (4) | IYYGDSLGLDY (7) |
| 25H3 | GYSFTDYNMN (1) | SINPYYGITTYNQTFKG (5) | IYYGDSLGLDY (7) |
| 25B7 | GYSFTDYNMN (1) | SINPYYGITSYNQTFKG (3) | IYYGDSLGLDY (7) |
| 25G1 | GYSFTGYFMN (2) | RINPYNGDTLYKQNFKD (6) | DGDGYYYAMDY (8) |
| 25G4 | GYSFTDYNMN (1) | SINPYYGITSYNQTFKG (3) | IYYGDSLGLDY (7) |
| 5H9 | GYSFTDYNMN (1) | SINPYYGITSYNQTFKG (3) | VYYGDSLGLDY (9) |
| N2F6 | GYSFTDYNMN (1) | SINPYYGITSYNQTFKG (3) | IYYGDSLGLDY (7) |

| Clone | CDRL1 (SEQ ID NO.) | CDRL2 (SEQ ID NO.) | CDRL3 (SEQ ID NO.) |
|---|---|---|---|
| 25A1 | SASSSVSYMH (10) | DTSKLAS (14) | QQWSSNPLT (16) |
| 25A10 | SASSSISYMH (11) | DTSKLAS (14) | QQWSSNPPT (17) |
| 25E4 | SASSSVSYMH (10) | DTSKLAS (14) | QQWSSNPPT (17) |
| 25E12 | SASSSVSYMH (10) | DTSKLAS (14) | QQWSSNPPT (17) |
| 25H3 | SASSSVSYMH (10) | DTSKLAS (14) | QQWSSNPLT (16) |
| 25B7 | SASSSKSYIH (12) | DTSKLAS (14) | QQWSSNPLT (16) |
| 25G1 | SASSSISYMH (11) | DTSKLAS (14) | HQRSSYPWT (18) |
| 25G4 | SASSSVSYMH (10) | DTSKLAS (14) | QQWSSNPPT (17) |
| 5H9 | SASSSVSYMY (13) | DTSNLAS (15) | QQWSSNPLT (16) |
| N2F6 | SASSSVSYMY (13) | DTSNLAS (15) | QQWSSNPLT (16) |

In one preferred embodiment of the disclosure, an antibody 25A1 or antigen-binding fragment thereof comprises the CDRH1 region comprises the amino acid sequence of SEQ ID NO: 1 or a substantially similar sequence thereof; the CDRH2 region comprises the amino acid sequence of SEQ ID NO: 3 or a substantially similar sequence thereof; the CDRH3 region comprises the amino acid sequence of SEQ ID NO: 7 or a substantially similar sequence thereof; the CDRL1 region comprises the amino acid sequence of SEQ ID NO: 10 or a substantially similar sequence thereof; the CDRL2 region comprises the amino acid sequence of SEQ ID NO: 14 or a substantially similar sequence thereof; and the CDRL3 region comprises the amino acid sequence of SEQ ID NO: 16 or a substantially similar sequence thereof. In one preferred embodiment, the antibody 25A1 comprises a heavy chain variable region comprising the amino acid sequence of SEQ ID NO: 19 or a substantially similar sequence thereof having at least about 90%, at least about 95%, at least about 98% or at least about 99% sequence identity. In one preferred embodiment, the antibody 25A1 comprises a light chain variable region comprising the amino acid sequence of SEQ ID NO: 20 or a substantially similar sequence thereof having at least about 90%, at least about 95%, at least about 98% or at least about 99% sequence identity.

In another aspect, the antibody according to the disclosure is preferably a humanized antibody. A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody.

In order to improve the binding affinity of the humanized antibody according to the disclosure, some amino acid residues in the human framework region are replaced by the corresponding amino acid residues in the species of CDRs; e.g. a rodent.

In one preferred embodiment, a humanized antibody or antigen-binding fragment thereof comprises a heavy chain variable region comprising the amino acid sequence selected from the group consisting of SEQ ID NOs: 21 to 23 or a substantially similar sequence thereof having at least about 90%, at least about 95%, at least about 98% or at least about 99% sequence identity. A humanized antibody or antigen-binding fragment thereof comprises a light chain variable region comprising the amino acid sequence selected from the group consisting of SEQ ID NOs: 24 to 26 or a substantially similar sequence thereof at least about 90%, at least about 95%, at least about 98% or at least about 99% sequence identity or a substantially similar sequence thereof.

In one preferred embodiment of the disclosure, a humanized antibody 25A1-B2B4AQT or antigen-binding fragment thereof comprises a heavy chain variable region comprising the amino acid sequence of SEQ ID NO: 27 or a substantially similar sequence thereof; and a light chain variable region comprising the amino acid sequence of SEQ ID NO: 28 or a substantially similar sequence thereof.

In one preferred embodiment of the disclosure, a humanized antibody 25A1-B5B6AQT or antigen-binding fragment thereof comprises a heavy chain variable region comprising the amino acid sequence of SEQ ID NO: 29 or a substantially similar sequence thereof; and a light chain variable region comprising the amino acid sequence of SEQ ID NO: 30 or a substantially similar sequence thereof.

In one preferred embodiment, the antibody according to the disclosure is a monoclonal antibody.

The antibodies of the present disclosure may be monospecific, bi-specific, or multispecific. Multispecific antibodies may be specific for different epitopes of one target polypeptide or may contain antigen-binding domains specific for more than one target polypeptide. The anti-α-toxin antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for α-toxin or a fragment thereof, and the other arm of the immunoglobulin is specific for a second therapeutic target or is conjugated to a therapeutic moiety.

In one preferred embodiment of the disclosure, the antibody or antigen-binding fragment thereof is conjugated with a therapeutic agent.

An example of the therapeutic agent is an antibiotic. Examples of the antibiotics include but are not limited to dactinomycin, bleomycin, mithramycin, anthramycin, streptozotocin, gramicidin D, or mitomycins.

In one preferred embodiment of the disclosure, the antibody or antigen-binding fragment thereof can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3.sup.rd ed. 1997)).

Techniques for the production of single chain antibodies or recombinant antibodies (U.S. Pat. Nos. 4,946,778, 4,816,567) can be adapted to produce antibodies to polypeptides of this disclosure. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

In one preferred embodiment of the disclosure, the antibody or antigen-binding fragment thereof is expressed on the surface of a cell. In one preferred embodiment, the cell is a T-cell.

The disclosure provides pharmaceutical compositions comprising the antibody or antigen-binding fragment thereof of the present disclosure. The pharmaceutical compositions of the disclosure are formulated with suitable diluents, carriers, excipients, and other agents that provide improved transfer, delivery, tolerance, and the like. The compositions may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present disclosure is used for treating a condition or disease associated with *Staphylococcal aureus* infection in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

The present disclosure provides a method for neutralizing α-toxin of *Staphylococcal aureus*, comprises administering to the subject an antibody of the present disclosure or an antigen-binding fragment thereof, or a pharmaceutical composition of the present disclosure. In one embodiment, the antibody binds α-toxin with KD ranging from $1\times10^{-8}$ to $1\times10^{-10}$ M; preferably, the KD ranges from $1\times10^{-8}$ to $1\times10^{-10}$ M; more preferably, the KD ranges from $1\times10^{-9}$ to $1\times10^{-10}$ M. In one embodiment, the method provides passive immunotherapy in the context of *S. aureus* infections.

The present disclosure provides a method for treating and/or preventing diseases and/or disorders caused by *Staphylococcal aureus* infection in a subject in need, comprising administering to the subject a pharmaceutical composition comprising the antibody or antigen-binding fragment thereof as mentioned above. In one embodiment, the *Staphylococcal aureus* infection is pneumonia.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause. As is understood by one skilled in the art, prevention or preventing need not achieve absolute (complete) block or avoidance of the conditions. Rather, prevention may achieve substantial (e.g., over about 50%) reduction or avoidance of the diseases or conditions to be prevented. Unless otherwise indicated herein, either explicitly or by implication, if the term "treatment" (or "treating") is used without reference to possible prevention, it is intended that prevention be encompassed as well.

The present disclosure provides a method for detecting α-toxin of *Staphylococcal aureus* in a sample comprising contacting the sample with the antibody or antigen-binding fragment thereof as mentioned above.

The present invention also provides a diagnostic agents or a kit for detecting α-toxin of *Staphylococcal aureus* in a sample, comprising an antibody or antigen-binding fragment thereof as mentioned above.

The anti-α-toxin antibody of the present disclosure may also be used to detect and/or measure α-toxin, or α-toxin-expressing cells in a sample, e.g., for diagnostic purposes. For example, an anti-α-toxin antibody, or fragment thereof, may be used to diagnose a condition or disease characterized by aberrant expression (e.g., over-expression, under-expression, lack of expression, etc.) of α-toxin. Exemplary diagnostic assays for α-toxin may comprise, e.g., contacting a sample, obtained from a patient, with an anti-α-toxin antibody of the disclosure, wherein the anti-α-toxin antibody is labeled with a detectable label or reporter molecule. Alternatively, an unlabeled anti-α-toxin antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure α-toxin in a sample include enzyme-linked immunosorbent assay (ELISA), radioimmunoassay (RIA), and fluorescence-activated cell sorting (FACS).

The following examples are provided to aid those skilled in the art in practicing the present disclosure.

EXAMPLES

Materials and Methods
Preparation of Antigen

The sequence of the non-toxic α-toxin mutant, $AT_{H35L}$, was constructed into a pET27b vector in frame with a C-terminal 6× His tag ((pET27b TAC1p α-hemolysin-6His). Alpha-toxin $AT_{H35L}$ was expressed and purified from E. coli BL21 strain. Briefly, a 750 mL fresh culture was grown at 37° C. with $OD_{600}$ of 0.67. IPTG (isopropyl-β-D-thiogalactopyranoside) was added to a final concentration of 0.25 mM to induce protein expression for 5 h at 30° C. The cells were then harvested and re-suspended in 100 ml of lysis buffer, followed by homogenizing by using a French press for 7 cycles. The cell lysate was clarified and then mixed with 2 ml of Ni-NTA. After two hours of binding, recombinant His-tag α-toxin $AT_{H35L}$ was eluted with 20~150 mM imidazole solution and dialyzed into phosphate buffer saline solution.

Immunization and Phage Library Generation

Eight to ten-week-old BABL/c mice were immunized with α-toxin $AT_{H35L}$ incomplete Freud's adjuvant via intraperitoneal injections every 2 weeks for 10 weeks. After two weeks of final injection, additional boosts were given daily for three days prior to sacrifice. An anti-AT scFv (a single-chain variable fragment) phage library was produced from mouse spleen cells. In brief, mouse spleen was homogenized and lysed with TRIZOL® reagent for RNA isolation and then cDNA was synthesized using SuperScript III™. The heavy chain variable region ($V_H$) and light chain variable region ($V_L$) of the DNA fragments were amplified by scFV primer set. To generate $V_L$-linker-$V_H$, the mixture of $V_L$, $V_H$, and flexible linker were amplified by PCR reaction. The $V_L$-linker-$V_H$ fragment was digested with Sfi, the cut inserts were ligated with phagemid vector. Ligation mixes were electroporated into *E. coli* TG1 competent cells to generate a phage library. The diversity was estimated to be $1.24\times10^9$ transformants.

Affinity Selection of Phage Library

Anti-AT antibodies were then panned from the phage library using both solution-based and plate-based methods. For solution-based panning, biotinylated-α-toxin was incubated with the phage library and streptavidin magnetic beads. After washing, the bound phage antibodies were eluted. The eluted phages were amplified and used for the next rounds of panning selection. A total of three rounds of panning were performed. For plate-based panning, α-toxin was coated onto microplates and incubated with the phage library, a total of three rounds of plate-based panning were performed. The phage particles were initially screened for their ability to bind α-toxin were analyzed using phage ELISA and the DNA was sequenced.

Phage ELISA

Ten microliters of individual phage overnight culture were grown in 150 μL of 2YT-A medium in 96-well microplate plate for 2 h at 37° C. The culture was then infected with 50 μL of helper phage ($2\times10^{10}$ PFU/ml) and incubated with shaking for another 2 h at 37° C. Fifty microliters of 2YT-A medium supplemented with 125 μg/ml kanamycin was added to culture plates and incubated with shaking overnight at 30° C. Culture supernatant containing phages of interest was obtained by centrifugation at 3,300×g for 30 minutes and used for phage ELISA screening. 100 μl of phage supernatant was added to AT-coated ELISA plates. Positive binders were detected with mouse anti-M13-HRP and TMB substrate. The absorbance was measured at 450 nm by ELISA plate reader.

Construction and Expression of the Full-Length Antibody

The light and heavy chains were amplified and treated with DraIII/BsiWI and MluI/NheI, respectively. The inserts were ligated into vectors containing light and heavy chain constant regions, and the constructs were transfected into F293 cells for expression. Purified full-length antibodies were tested and ranked by $IC_{50}$ in the neutralization of AT-induced A549 cytolysis.

SPR Binding to Recombinant α-Toxin

Surface plasma resonance (SPR) was used to determine the binding kinetics of 25A1 to recombinant AT. Briefly, approximately 200 response units (RU) of 25A1 were immobilized onto CMS chips using standard amine coupling procedures. Subsequently, serially diluted AT at concentrations of 1.5625, 3.125, 6.25, 12.5, 25 and 50 nM were injected at 30 μL/min for 180 seconds and dissociated for 480 seconds. The kinetic parameters ($K_{on}$ and $K_{off}$) and affinities ($K_D$) were calculated using the Biacore T100 evaluation software 2.0 with a 1:1 interaction binding model.

Humanization of Parental Mouse Monoclonal Antibody 25A1

Humanization was conducted by the complementarity-determining region (CDR) grafting. Mouse 25A1 protein sequence was aligned to human germline sequences to identify human sequence with high sequence identity, sequences from light chain family IGVK3-11 and heavy chain family IGHV1-2 were adopted as the framework sequences. In addition to CDRs grafting. The sequences were further analyzed for potential free cysteine, deamination, lysine clipping, and protease cutting sites formation. The chimeric and humanized 25A1 antibodies were expressed transiently in F293 cells and purified.

Neutralization of α-Toxin-Induced A549 Cytolysis

Functional assay for the anti-AT antibodies was established. A549 cells were seeded in microplates at $2\times10^4$ cells/well and cultured at 37° C. with 5% $CO_2$ overnight. The next day, the medium was removed and the cells were washed with medium. Purified antibodies were added to the cells at 0.4, 4, and 40 μg/mL and co-incubated with 8 μg/mL of AT. At the end of incubation, cell viability was analyzed using a colorimetric MTT assay kit. The results were determined with the background absorbance at $OD_{690}$ nm and subtracted from the $OD_{570}$ nm measurement (FIG. 1).

Rabbit Erythrocyte Lysis Assay

*S. aureus* crude supernatants were collected from 3 ml of tryptic soy broth (TSB) overnight culture by centrifugation at 6000 rpm for 10 minutes. The supernatants from various strains were then filter sterilized and stored at −80° C. until further use.

RBC cells were collected using iodixanol gradient solution and the final cell pellet was resuspended in balanced salt medium (0.85% NaCl, 10 mM HEPES, pH7.4) and kept at 4° C. The ability of the antibodies to neutralize AT-induced rabbit RBC hemolysis was evaluated. Specifically, 25 μl of each antibody at the concentration of 100, 50, 25, 12.5, 6.25, 3.125, and 1.56 and 0.78 was added to the well together with 100 μl of 10% rabbit RBC, followed by adding 25 μl of 1:8~1:16-diluted *S. aureus* culture supernatant from various strains. After incubation of 45~60 minutes at 37° C., plates were centrifuged for 5 min, 50 μl of the supernatant was removed gently to a new microtiter plate, and absorbance was read at 450 nm. Antibody potency is defined as the antibody concentration at which 50% inhibition of α-toxin-induced hemolysis was achieved. 2% TritonX-100 served as 100% hemolysis control. Inhibition of hemolysis was calculated as ((OD450 of 2% TritonX-100–OD450 of test antibody)/OD450 of 2% TritonX-100)×100%.

Murine Bacteremia Model

Groups of 6 female BALB/c or CD-1 mice were passively immunized by intraperitoneal injection of control antibody or 25A1 and then challenged 24h later by intravenous (i.v.) injection of 90% lethal dose of S. aureus BAA-1717, or by intraperiotoneal injection of the ATCC29213 strain. Animal mortality was observed for 10 consecutive days. Survival was recorded and results were analyzed using GraphPad Prism. Statistical significance analysis was performed with Kaplan-Meir survival analysis with Log-rank (Mantel-Cox) and Gehan-Breslow-Wilcoxon tests.

Murine Pneumonia Model

Groups of ten 7 to 9-week-old female C57BL/6J mice (Jackson Labs, Bar Harbor, Mich.) were passively immunized by intraperitoneal injection of SYN100 (25A1-B5B6AQT) and then challenged 24 h later by intranasal (IN) administration with a lethal dose of each S. aureus clinical isolate. Vancomycin was administered subcutaneously at 2h post infection. Animals were monitored for survival with a census taken 3 times per day for 7 days following infection. Survival was recorded and results were analyzed using GraphPad Prism. Statistical significance analysis was performed with Kaplan-Meir survival analysis with Log-rank (Mantel-Cox) and Gehan-Breslow-Wilcoxon tests.

Rabbit Pneumonia Model

Groups of three to nine male New Zealand rabbits were treated with different dosages of SYN100 24 hours prior to infection. The inoculum sizes of the infections were kept within $2.9-5.2 \times 10^7$ CFU/rabbit. Linezolid, if used, was administered at four hours post infection by subcutaneous injection at 50 mg/kg/8h. Animals were monitored for survival with a census taken 2 times per day for 7 days following infection. Survival was recorded and results were analyzed using GraphPad Prism. Statistical significance analysis was performed with Kaplan-Meir survival analysis with Log-rank (Mantel-Cox) and Gehan-Breslow-Wilcoxon tests.

Example 1 Isolation of Anti-α-Toxin Antibody

BABL/c mice were immunized with recombinant AT specifically inactivated by introducing the H35L mutation. We then constructed a single-chain variable fragment (scFv) phage library and panned with AT purified from S. aureus. After three rounds of panning, 29 unique binders were identified, produced, and tested for the neutralization activity against AT-induced A549 cytolysis. The results showed that only 10 (25A1, 25A10, 25E4, 25E12, 25H3, 25B7, 25G1, 25G4, 5H9, and N2F6) of the 29 purified antibodies inhibited A549 cytolysis when the antibody was used at 40 µg/mL (FIG. 1). Neutralization activities of the 10 antibodies are summarized in Table 3. The antibodies were then converted to full-length antibodies and further characterized for binding and confirmed for neutralization activity. CDR sequences of the 10 clones are shown in Table 2 (as shown above). A comparison of CDR sequences revealed that 9 of the 10 inhibitory antibodies were nearly identical in amino acid sequence. Five of them (25A10, 25A1, 25E12, 25H3, and 25E4) had very similar functional activity in the neutralization of AT-induced A549 cytolysis. Clone 25A1 was selected based on binding and functional activity.

TABLE 3

| Clone | Sequence analysis | Cytotoxicity | Clone | Sequence analysis | Cytotoxicity |
|---|---|---|---|---|---|
| aN2-25A10 | √ | ++ | aSTAPH N2F6 | √ | + |
| aN2-25D5 | √ | − | aSTAPH N2H1 | √ | − |
| aN3-12.5A7 | √ | − | aSTAPH N2A2 | √ | − |
| aN2-25D8 | √ | − | aSTAPH N2F11 | √ | − |
| aN3-12.5E6 | √ | − | aSTAPH N2E10 | √ | − |
| aN2-25G12 | √ | − | aSTAPH N2B6 | √ | − |
| aN3-25F2 | √ | − | aN2-25A1 | √ | ++ |
| aN3-25G1 | √ | + | aSTAPH N2D12 | √ | − |
| aN3-12.5D2 | √ | − | H9395 R4A8 | √ | − |
| aN2-25B8 | √ | − | aN2-25E12 | √ | ++ |
| H9395 R4B11 | √ | − | aN2-25H3 | √ | ++ |
| aN2-25B7 | √ | + | aSTAPH N2D1 | √ | − |
| aN3-12.5119 | √ | + | aN2-25E4 | √ | ++ |
| aSTAPH N2B11 | √ | − | aN2-25G4 | √ | + |
| aSTAPH N2B10 | √ | − | | | |

Example 2 the High-Affinity Binding of 25A1 to Recombinant α-Toxin

Figure 2:
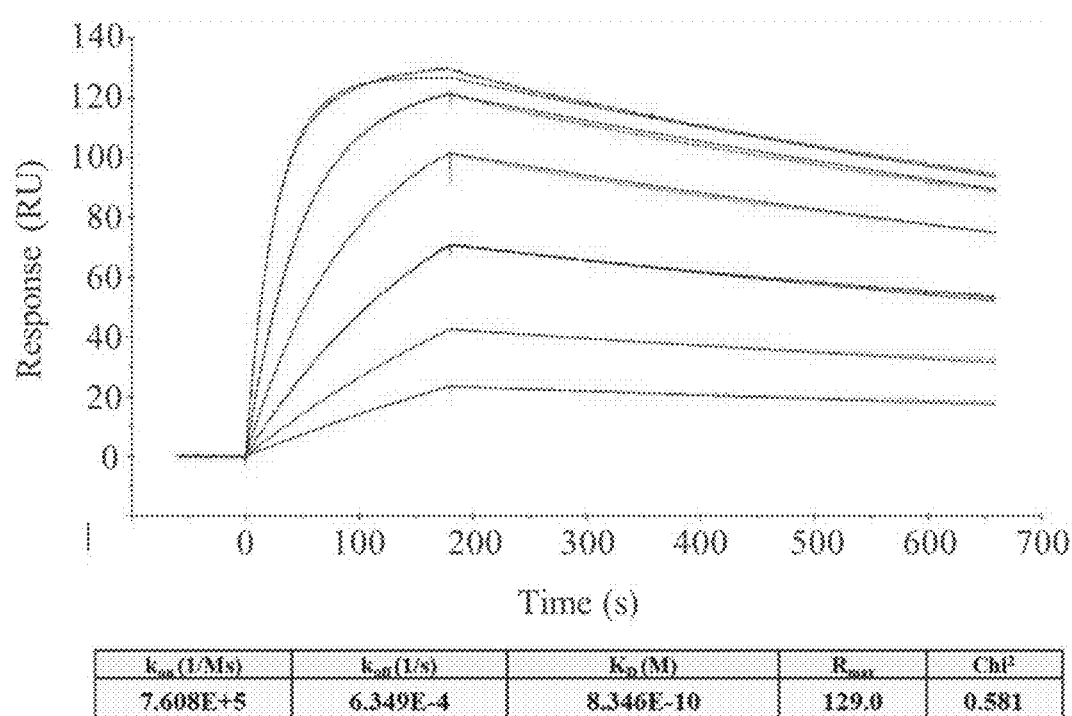
FIG. 2: Mouse 25A1 monoclonal antibody binds to α-toxin. Antigen binding profiles of 25A1 captured on an active flow cell on a Biacore T100. The different lines represent the binding response of 25A1 toward α-toxin at various concentrations from 1.56~50 nM.

The affinity of 25A1 for recombinant AT was evaluated by surface plasma resonance. As shown in FIG. 2, 25A1 binds α-toxin with KD of $8.346 \times 10^{-10}$ M. The association and disassociation constants were $7.608 \times 10^5$ $M^{-1}s^{-1}$ and $6.349 \times 10^{-4}$ $s^{-1}$ respectively. This data indicates that 25A1 has a high affinity for AT.

Example 3 Engineering and Characterization of Humanized 25A1

Figure 3B:
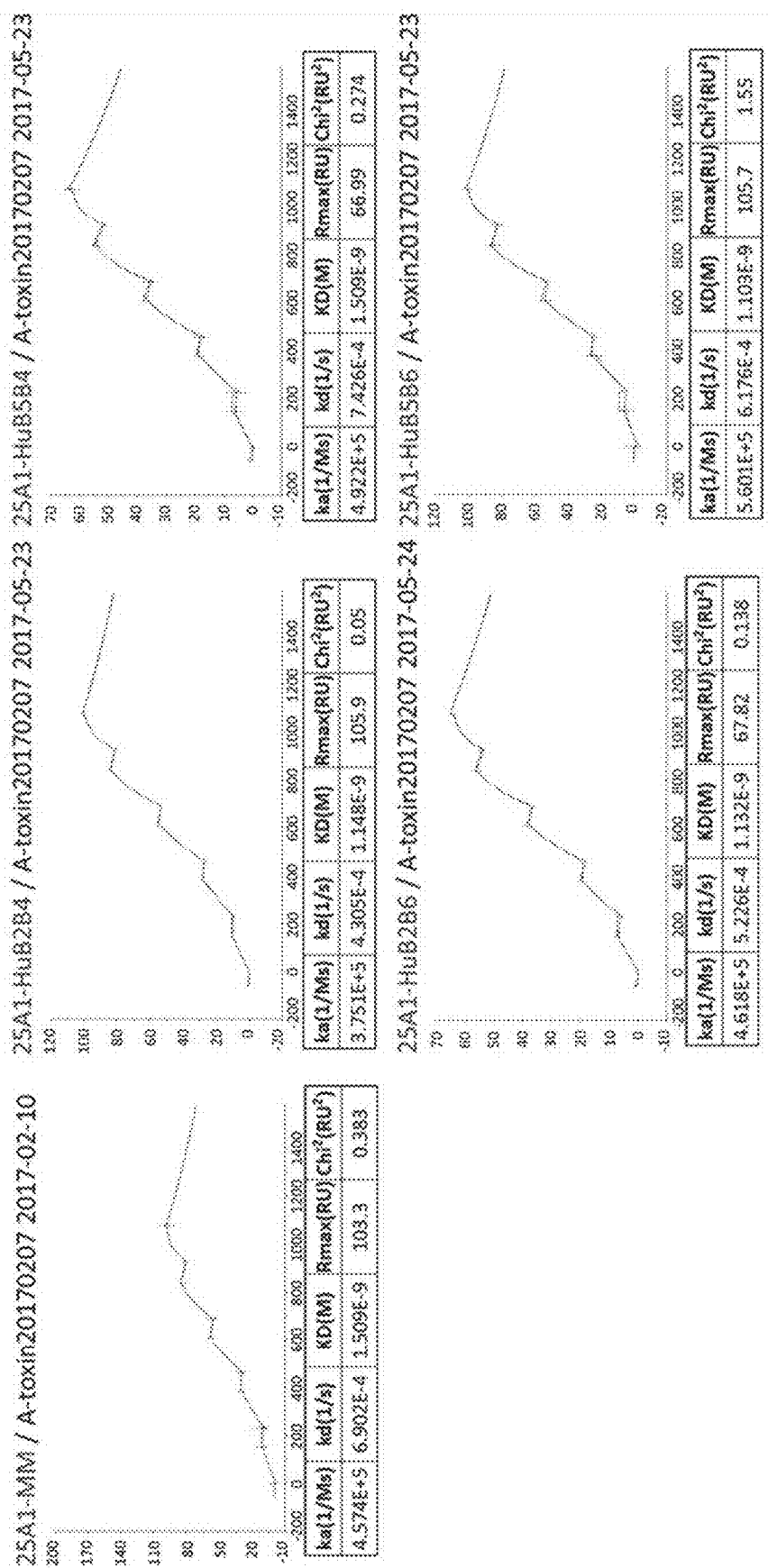
FIG. 3(B) SPR sensorgrams of the binding kinetics of antibodies binding to recombinant α-toxin. The binding kinetics was measured by the single-cycle kinetic method by BIAcore T200.

To reduce immunogenicity introduced with murine antibodies, we chose to graft the CDRs of the murine 25A1 antibody onto human framework IGVK3-11*01F for light chain and IGHV1-2*02F for heavy chain because of their high sequence and conformational to murine 25A1. Different combinations of back-mutations were generated and tested for antigen binding. Based on binding affinities and number of back-mutations, two variants of heavy chain 25A1-VHB2 and 25A1-VHB5 and 2 of light chain 25A1-VLB4 and 25A1-VLB6 were selected to build variants 25A1-HuB2B4, 25A1-HuB5B4, 25A1HuB2B6, and 25A1-HuB5B6. Sequence variations of the antibody after CDR grafting and back-mutation are shown in FIG. 3(A). The binding kinetic ($K_D$) of humanized antibodies 25A1-HuB2B4, 25A1-HuB5B4, 25A1HuB2B6, and 25A1-HuB5B6 toward recombinant α-toxin were determined by forteBio to be $1.1 \times 10^{-9}$ M, $1.5 \times 10^{-9}$ M, $1.1 \times 10^{-9}$ M, and $1.1 \times 10^{-9}$ M, respectively, which are highly similar to the $K_D$ of the parental murine antibody 25A1, $1.5 \times 10^{-9}$ M (FIG. 3(B)).

We then selected 25A1-B2B4 and 25A1-B5B6 for the sequence liability check. A potential glycosylation site was identified at N61 in heavy chain CDR2 region (FIG. 3(C)). N61 was therefore mutated to alanine to avoid unnecessary complications from extra glycosylation; the N61A mutant clones were named as 25A1-B2B4AQT and 25A1-B5B6AQT.

Example 4 Neutralization of α-Toxin-Induced Rabbit Red Blood Cell Hemolysis

Figure 4:
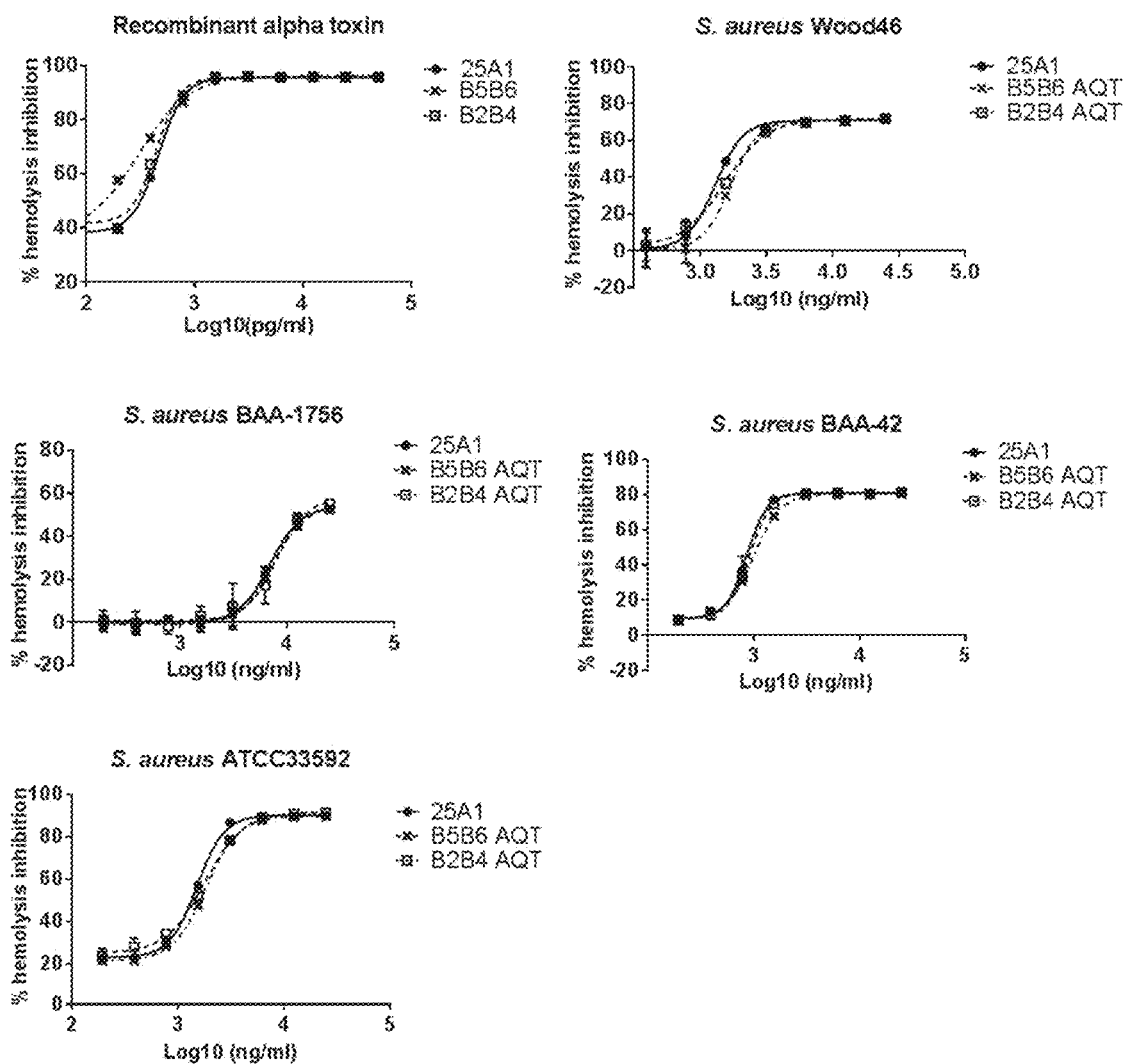
FIG. 4: 25A1, 25A1-B2B4AQT, and 25A1-B5B6AQT inhibit recombinant α-toxin or native α-toxin-induced lysis of rabbit RBC cells. Serial dilutions of antibodies (100, 50, 25, 12.5, 6.25, 3.125, 1.56 and 0.78 mg/mL) were incubated with recombinant α-toxin (400 ng/ml) or crude bacteria supernatant (1:8~1:16 dilution) along with rabbit RBC. Hemolysis is measured by the amount of hemoglobin release in the supernatant. Percent hemolysis inhibition was calculated as ((OD450 of 2% TritonX-100−OD450 of test antibody)/OD450 of 2% TritonX-100)×100%.

Humanized 25A1, 25A1-B2B4AQT, and 25A1-B5B6AQT, were then produced and tested for inhibition of native α-toxin-induced rabbit RBC hemolysis. In brief, bacteria supernatant from stationary phase (overnight culture) was collected from five S. aureus clinical strains (BAA-1717, BAA-1756, ATCC33592, BAA-42, and Wood46) and added to rabbit RBC along with various anti-AT antibodies across the concertation range of 0.195 to 25µg/mL. The percentage inhibition of RBC hemolysis induced with recombinant and native α-toxin from five tested strains are shown in FIG. 4. Antibodies 25A1, 25A1-B2B4AQT, and 25A1-B5B6AQT were able to bind native α-toxin from the strains tested, and exhibited~50%-90% inhibition of various native α-toxin-mediated RBC lysis. $IC_{50}$ values of 25A1, 25A1-B2B4AQT, and 25A1-B5B6AQT for inhibiting recombinant α-toxin-induced hemolysis were 462.3, 442.9 and 304.2 pg/mL; for ATCC33592 were 1518, 1801 and 1830 ng/mL; for BAA-1756 were 6913, 7956 and 7322 ng/mL, for Wood46 were 1299, 1707 and 1537 ng/mL and for BAA-42 were 860.6, 910.8 and 996.3 ng/mL, suggesting both 25A1-B2B4AQT and 25A1-B5B6AQT retained comparable inhibitory ability to 25A1.

Figure 5:
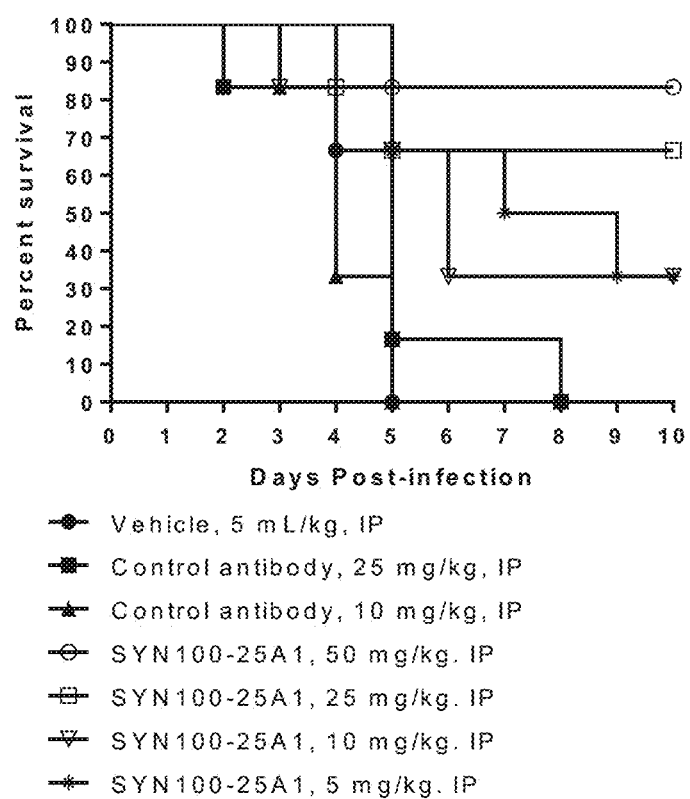
FIG. 5: Kaplan-Meir survival curve for S. aureus BAA-1717 infected mice administered SYN100. Mice were inoculated intravenously with USA300 MRSA, BAA-1717 with an inoculum size at $8×10^7$ CFU/mouse on Day 0. 25A1 was administered intraperitoneally (IP) at 50, 25, 10 and 5 mg/kg twenty-four (24) hours before infection. The control antibody at 25 and 10 mg/kg was also administered intraperitoneally 24 hours before infection. Animal mortality was monitored for 10 days. Survival of 50 percent or more (50%) of the animals relative to the vehicle control group indicated significant anti-infective activity.
Figure 6:
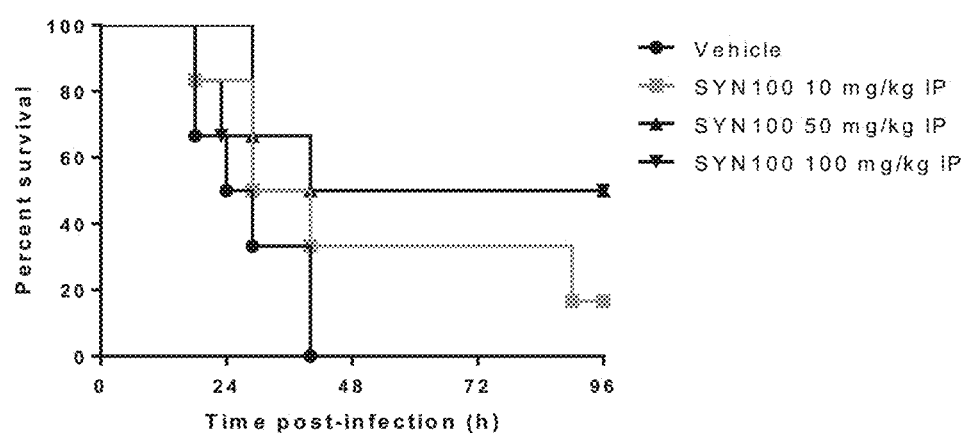
FIG. 6: Kaplan-Meir survival curve for S. aureus ATCC29213-infected mice administered with SYN100. CD-1 mice were inoculated intraperitoneally with ATCC29213 at an inoculum size of $2.0×10^7$ CFU/mouse on Day 0. SYN100 was administered intraperitoneally (IP) at 100, 50, and 10 mg/kg to three groups of mice twenty-four (24) hours before infection. Survival of infected animals was monitored for 4 days.

Example 5 SYN100 Increases Survival Rate in Murine Bacteremia and Pneumonia Model S. aureus is a common cause of sepsis, a systemic inflammation with multiple organ dysfunctions. AT plays an important role in sepsis model since S. aureus hla mutants display delayed time-to-death and increase survival in a mouse sepsis model. We therefore tested 25A1 for the ability to protect mice against S. aureus infection. As shown in FIG. 5, death of the vehicle control was observed between Day 2 and Day 5. By contrast, 25A1 treated groups exhibited increased survival rates; the overall survival rates for the 50, 25, 10 and 5 mg/kg dose groups were 83%, 67%, 33% and 50% (FIG. 5), this data indicated that prophylaxis with 25A1 provides the protection against bacteremia infection. In another murine sepsis model established with methicillin-sensitive S. aureus strain ATCC29213, SYN100 also exhibited protection as prophylactic therapy at 100, 50, and 10 mg/kg (FIG. 6). Though with some variation among different strains, these observed efficacy support the prophylactic use of SYN100 in S. aureus sepsis and bacteremia.

Figure 7:
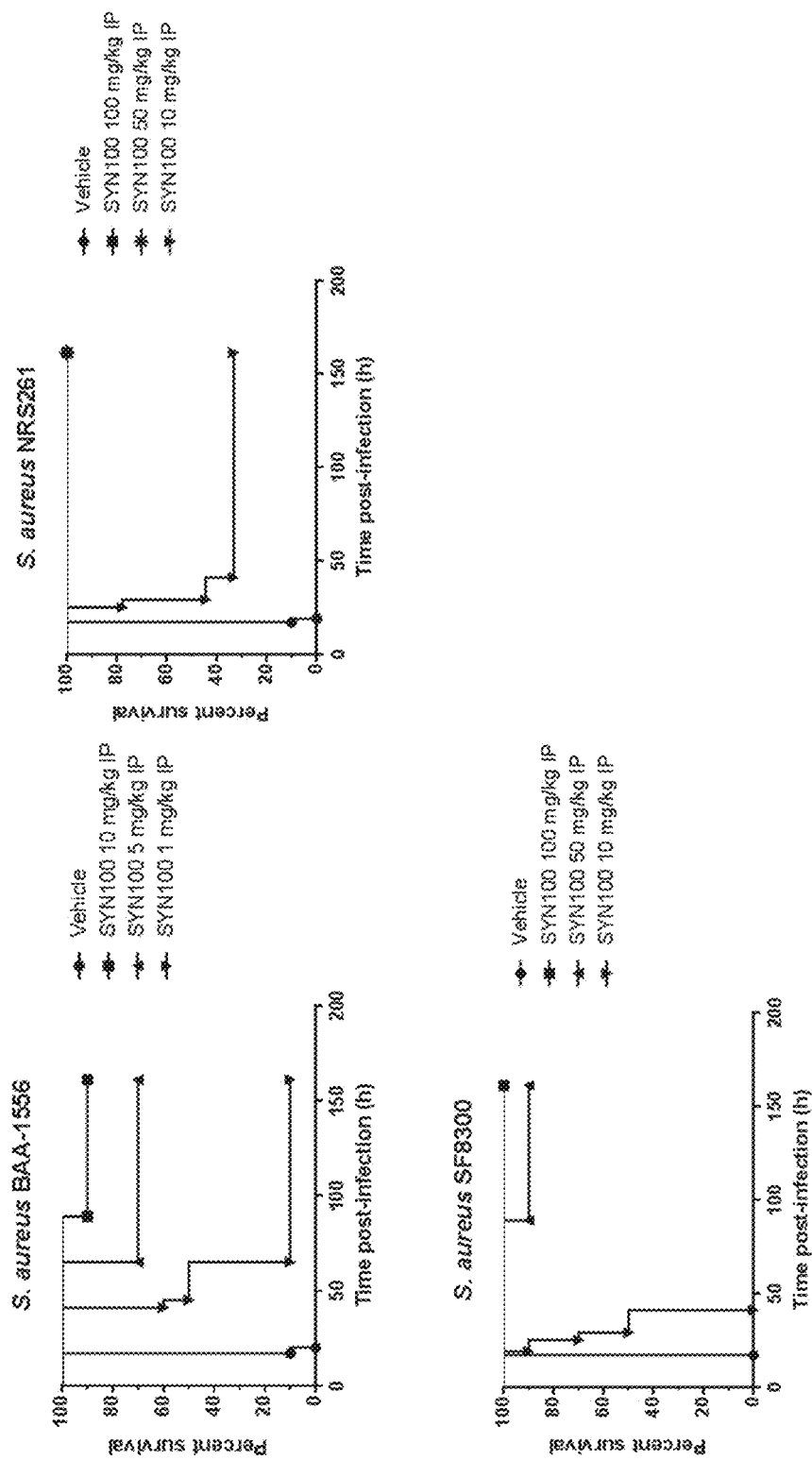
FIG. 7: Kaplan-Meir survival curves for S. aureus BAA-1556, NRS261, and SF8300 infected mice administered SYN100. SYN100 prophylaxis increases the survival rate in a murine pneumonia model. C57BL/6J mice were inoculated intranasally with BAA-1556 with an inoculum size at $1.62×10^7$ CFU/mouse; NRS261 with an inoculum size at $3.3×10^7$ CFU/mouse or SF8300 with an inoculum size at $2.82×10^7$ cfu on Day 0. SYN100 was administered intraperitoneally (IP) at 10, 5, and 1 mg/kg for BAA-1556 infected mice or 100, 50, and 10 mg/kg twenty-four (24) hours before infection. Survival of infected animals was monitored for 7 days.

Since S. aureus is frequent cause of ventilator-associated pneumonia in patients, the protective efficacy of SYN100 was evaluated in S. aureus-induced murine pneumonia models. Infection was induced by intranasal challenge with three S. aureus clinical isolates BAA1556 (USA300), SF8300 (USA300), or NRS261 (USA200) 24 hour following administration of SYN100. In acute pneumonia model, death of the vehicle control group occurred between 18-20 hr following challenge. By contrast, prophylaxic administration of SYN100 resulted in significant extension of survivorship in all three models, demonstrating that SYN100 can provide protection against diverse S. aureus clinical isolates (FIG. 7).

Figure 8:
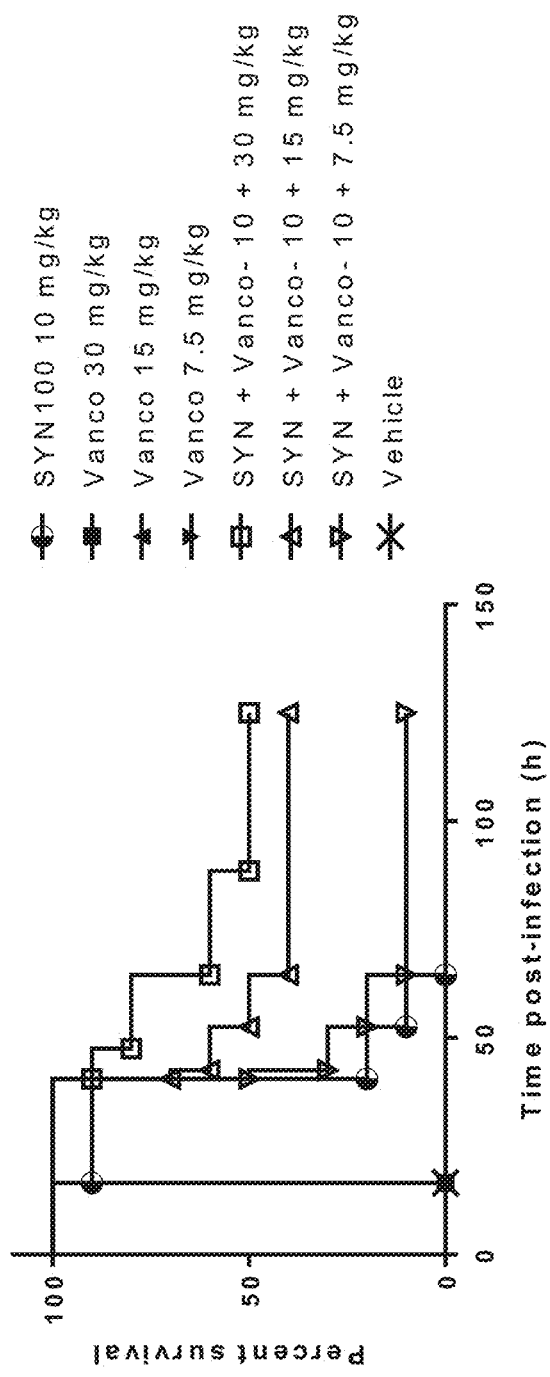
FIG. 8: Kaplan-Meir survival curve for S. aureus NRS261-infected mice administered with SYN100, and/or vancomycin. C57BL/6J mice were inoculated intranasally with NRS261 at an inoculum size of $5.0×10^7$ CFU/mouse on Day 0. SYN100 was administered intraperitoneally (IP) at 10 mg/kg to four groups of mice twenty-four (24) hours before infection. Vancomycin was administered at 30, 15, and 7.5 mg/kg two hours post infection. Three groups of mice received both vancomycin and SYN100. Survival of infected animals was monitored for 5 days.

In a subsequent experiment, how SYN100 works in relation to antibiotic treatment was tested in the murine NRS261 pneumonia model. Vancomycin is commonly prescribed to treat MRSA infections in the clinic; we therefore tested efficacy of SYN100 in combination with vancomycin treatment as standard of care. As shown in FIG. 8, neither SYN100 at 10 mg/kg nor vancomycin at up to 30 mg/kg significantly extended survival of the mice. Nevertheless, the three groups of mice that received both SYN100 and vancomycin exhibited dose-dependent survival, which is highly indicative of synergy between SYN100 and vancomycin.

Example 6 SYN100 Increases Survival Rate in Rabbit Pneumonia Model

Figure 9:
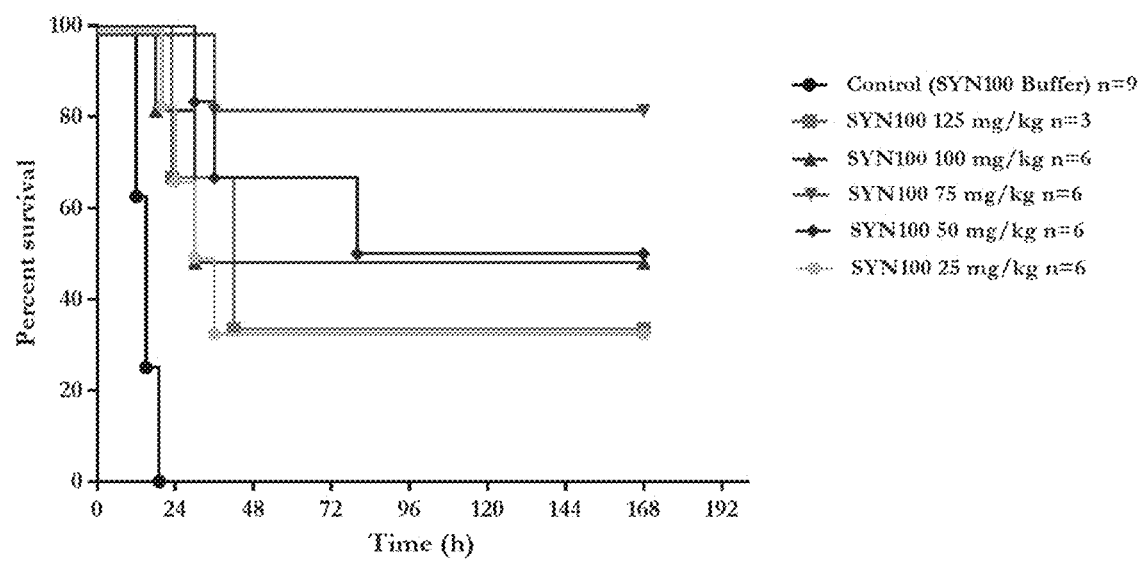
FIG. 9: Kaplan-Meir survival curve for S. aureus ST20120426 infected rabbits administered with SYN100. New Zealand rabbits were inoculated intranasally with ST20120426 at inoculum sizes between $3.2-5.2×10^7$ CFU/rabbit on Day 0. SYN100 was administered intravenously at 125, 100, 75, 50, and 25 mg/kg twenty-four (24) hours before infection. Survival of infected animals was monitored for 7 days.

In many ways, rabbits are more suitable model organisms for S. aureus infections than mice. We thus tested efficacy of SYN100 in a rabbit pneumonia model established with a hospital-acquired MRSA strain, ST20120426. ST20120406 is a highly virulent strain that secrets relatively large amounts of α-toxin, causing the control animals to collapse within 24h. As shown in FIG. 9, all dosages of SYN100 tested on this model, ranging from 25 to 125 mg/kg, provided significant extension of survivorship, thus representing yet another proof for the utility of SYN100 in S. aureus pneumonia.

Figure 10:
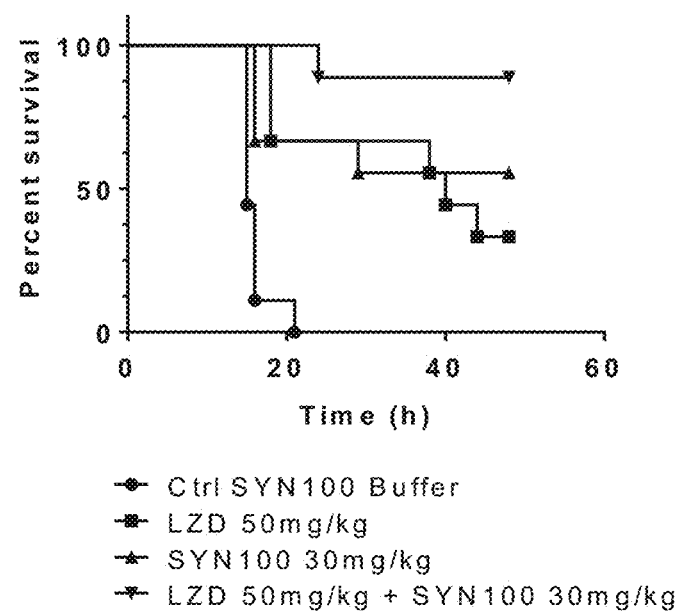
FIG. 10 (A) Kaplan-Meir survival curve for S. aureus ST20120426 infected rabbits administered with SYN100 and/or linezolid. New Zealand rabbits were inoculated intranasally with ST20120426 at inoculum sizes between $2.9-4.1×10^7$ CFU/rabbit on Day 0. SYN100 was administered intravenously at 30 mg/kg twenty-four (24) hours before infection. Linezolid was administered 4 hours post infection at 50 mg/kg/8h. Survival of infected animals was monitored for 48 hours.
Figure 10:
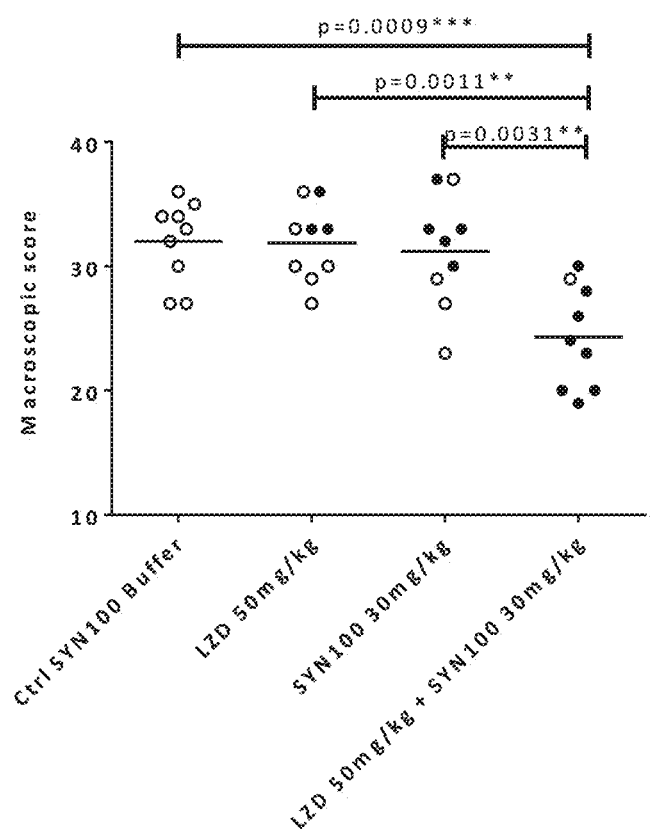
Figure 10:
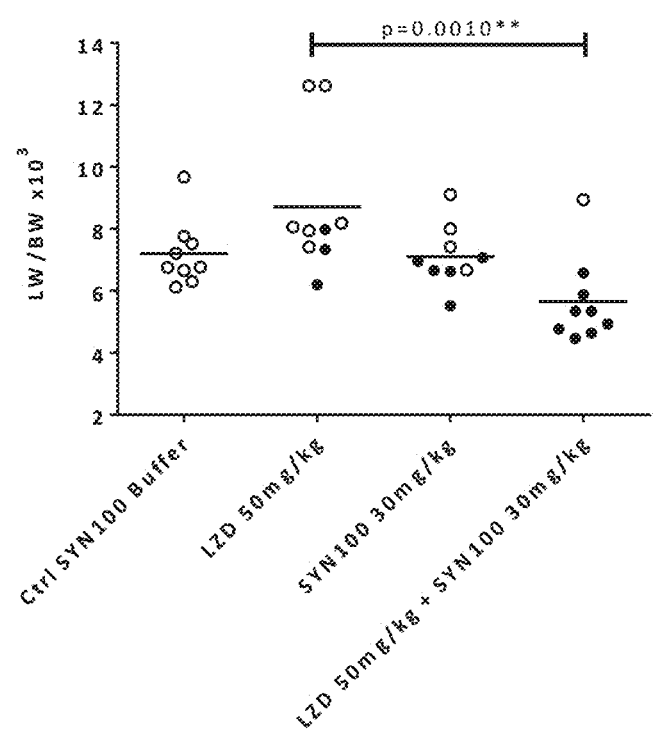
Figure 10:
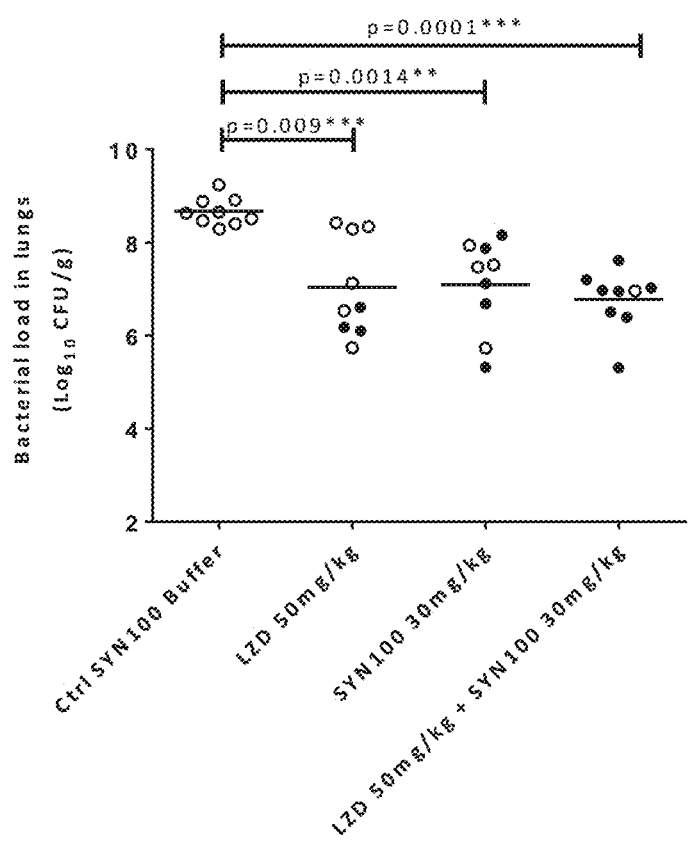

Co-treatment of SYN100 with an antibiotic was further explored in the ST20120426 rabbit pneumonia model. Data in FIG. 10A shows that single treatment with SYN100 at 30 mg/kg and linezolid (LZD) at 50 mg/kg/8h resulted in 56% and 33% overall survival, respectively, while the group receiving both SYN100 and LZD had 89% survival. Further examination of the lung tissues revealed that only the combination treatment group had significantly reduced lung swelling, bacterial load, and appeared more normal in macroscopic appearances. LZD inhibits the initiation of protein synthesis in bacteria and has been shown to be equally effective as vancomycin, which is a cell wall synthesis blocker. Taken together, these results suggest that SYN100 complements the actions of both antibiotics and provides further protection against MRSA infections in an additive or synergistic fashion.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

We claim:

1. An antibody or antigen-binding fragment thereof that specifically binds to an epitope in α-toxin of Staphylococcal aureus or a fragment thereof; wherein the antibody or antigen-binding fragment thereof comprises complementarity determining regions (CDRs) of a heavy chain variable region and complementarity determining regions of a light chain variable region, wherein the complementarity determining regions of the heavy chain variable region comprise CDRH1, CDRH2 and CDRH3 regions, and the complementarity determining regions of the light chain variable region comprise CDRL1, CDRL2 and CDRL3 regions, and wherein:

the CDRH1 region comprises the amino acid sequence consisting of SEQ ID NO: 1; the CDRH2 region comprises the amino acid sequence consisting of SEQ ID NO: 3; the CDRH3 region comprises the amino acid sequence consisting of SEQ ID NO: 7; and the CDRL1 region comprises the amino acid sequence consisting of SEQ ID NO: 10; the CDRL2 region comprises the amino acid sequence consisting of SEQ ID NO: 14; the CDRL3 region comprises the amino acid sequence consisting of SEQ ID NO: 16.

2. The antibody or antigen-binding fragment thereof according to claim 1, wherein the antibody is a mammalian antibody.

3. The antibody or antigen-binding fragment thereof according to claim 1, wherein the antibody or antigen-binding fragment thereof comprises a heavy chain variable region comprising the amino acid sequence of SEQ ID NO: 19; and a light chain variable region comprising the amino acid sequence of SEQ ID NO: 20.

4. The antibody or antigen-binding fragment thereof according to claim 1, wherein the antibody or antigen-binding fragment thereof comprises a heavy chain variable region comprising the amino acid sequence consisting of SEQ ID NOs: 21 to 23; and a light chain variable region comprising the amino acid sequence consisting of SEQ ID NOs: 24 to 26.

5. The antibody or antigen-binding fragment thereof according to claim 1, wherein the antibody or antigen-binding fragment thereof comprises a heavy chain variable region comprising the amino acid sequence of SEQ ID NO: 27; and a light chain variable region comprising the amino acid sequence of SEQ ID NO: 28.

6. The antibody or antigen-binding fragment thereof according to claim 1, wherein the antibody or antigen-binding fragment thereof comprises a heavy chain variable region comprising the amino acid sequence of SEQ ID NO: 29; and a light chain variable region comprising the amino acid sequence of SEQ ID NO: 30.

7. The antibody or antigen-binding fragment thereof according to claim 1, wherein the antibody is a monoclonal antibody, chimeric antibody, humanized antibody or human antibody.

8. A pharmaceutical composition comprising the antibody or antigen-binding fragment thereof according to claim 1 and pharmaceutically acceptable carriers or excipients.

9. A method for neutralizing α-toxin of Staphylococcal *aureus* in a subject in need, comprises administering to the subject the antibody or antigen-binding fragment thereof according to claim 1.

10. The method of claim 9, wherein the antibody binds α-toxin with KD ranging from $1\times10^{-7}$ to $1\times10^{-10}$ M.

11. The method of claim 9, wherein the method provides passive immunotherapy in the context of *S. aureus* infections.

12. A method for treating, prophylactic treating and/or preventing diseases and/or disorders caused by Staphylococcal *aureus* infection in a subject in need, wherein the method comprises administering to the subject the antibody or antigen-binding fragment thereof according to claim 1.

13. The method of claim 12, wherein the diseases and/or disorders caused by Staphylococcal *aureus* infection is pneumonia.

14. A method for detecting α-toxin of Staphylococcal *aureus* in a sample, wherein the method comprises contacting the sample with the antibody or antigen-binding fragment thereof according to claim 1.

15. A kit for detecting α-toxin of Staphylococcal *aureus* in a sample, wherein the kit comprises the antibody or antigen-binding fragment thereof according to claim 1.

* * * * *